US007262163B2

(12) United States Patent
McLaughlin et al.

(10) Patent No.: US 7,262,163 B2
(45) Date of Patent: *Aug. 28, 2007

(54) SHORT AMPHIPATHIC PEPTIDES WITH ACTIVITY AGAINST BACTERIA AND INTRACELLULAR PATHOGENS

(75) Inventors: Mark L. McLaughlin, Baton Rouge, LA (US); Thomas S. Yokum, Greensboro, NC (US); Frederick M. Enright, Baton Rouge, LA (US); Philip H. Elzer, Baton Rouge, LA (US); Robert P. Hammer, Baton Rouge, LA (US)

(73) Assignee: Board of Supervisors of Louisiana State University and Agricultural and Mechanical College, Baton Rouge, LA (US)

( * ) Notice: Subject to any disclaimer, the term of this patent is extended or adjusted under 35 U.S.C. 154(b) by 478 days.

This patent is subject to a terminal disclaimer.

(21) Appl. No.: 10/414,342

(22) Filed: Apr. 14, 2003

(65) Prior Publication Data
US 2004/0059088 A1 Mar. 25, 2004

Related U.S. Application Data

(63) Continuation of application No. 09/019,490, filed on Feb. 5, 1998, now Pat. No. 6,566,334.

(60) Provisional application No. 60/183,014, filed on Feb. 6, 1997.

(51) Int. Cl.
*A61K 38/03* (2006.01)
*C07K 4/00* (2006.01)

(52) U.S. Cl. ............................. 514/2; 514/14; 514/15; 514/16; 514/17; 530/326; 530/327; 530/328; 530/329

(58) Field of Classification Search .................. 514/14, 514/15, 16; 530/326, 327, 328, 329
See application file for complete search history.

(56) References Cited

U.S. PATENT DOCUMENTS

| | | | | |
|---|---|---|---|---|
| 4,230,061 | A | 10/1980 | Roberts et al. | 114/74 A |
| 5,038,960 | A | 8/1991 | Seery | 220/403 |
| 5,072,623 | A | 12/1991 | Hendershot | 73/49.2 |
| 5,789,542 | A | 8/1998 | McLaughlin et al. | 530/326 |
| 6,566,334 | B1 * | 5/2003 | McLaughlin et al. | 514/14 |

FOREIGN PATENT DOCUMENTS

| DE | 4326344 | 2/1995 |
|---|---|---|
| WO | WO9012866 | 11/1990 |
| WO | WO9301723 | 2/1993 |

OTHER PUBLICATIONS

Smythe et al. "The Molten Helix: Effects of Solvation on the .alpha.- to 310-Helical Transition" J. Am. Chem. Soc. 1995, 117, 5445-5452.*

Alexopoulos, C. et al., "The Position of the LysN$^e$H$_2$ Grafted Antigens Along the Sequential Oligopeptide Carrier, Ac-(Aib-Lys-Aib-Gly)$n$ (SOC$n$-II), Influences the Antibody Recognition: Application to the Sm Main Autoimmune Epitope," Biopolymers, vol. 54, pp. 1-10 (2000).

Araya et al., "Temporal Development or Protective Cell-Mediated and Humoral Immunity in BALB/c Mice Infected with Brucella abortus," Journal of Immunology, vol. 53, pp. 3330-3337 (1989).

Barr et al., "Activity of Lytic Peptides Against Intracellular Trypanosoma cruzi Amastigotes in vitro and Parasitemias in Mice," Journal of Parasitology, vol. 81, No. 6, pp. 974-978 (1995).

Basu, G. et al., "Conformational Preferences of Oligopeptides Rich in $\alpha$-Aminiosobutyric Acid. I. Observation of a $3_{10}$/ $\alpha$-Helical Transition upon Sequence Permutation," Biopolymers, vol. 31, pp. 1763-1774 (1991).

Becker,C.L., "The Design, Synthesis and Structure-Function Studies of Highly Repetitive Amphiphilic Antibacterial Peptides and the Synthesis of Benz[f]indene for the Preparation of Novel Metallocenes," Louisiana State University (Baton Rouge) PhD Dissertation (May 1994) (unpublished).

Benedetti et al., "Peptaibol Antibiotics: A Study on the Helical Structure of the 2-9 Sequence of Emerimicins III and IV," Proceedings of the National Academy of Sciences, vol. 79, pp. 7951-7954 (1982).

Bessalle, R. et al., "Structure-Function Studies of Amphiphilic Antibacterial Peptides," J. Med. Chem., vol. 36, pp. 1203-1209 (1993).

Blondelle et al., Design of Model Amphipathic Peptides Having Potent Antimicrobial Activities, Biochemistry, vol. 31, pp. 12688-12694 (1992).

Bundgaard, H., "Prodrug Derivatives of Thyrotropin-Releasing Hormone and Other Peptides," Biochem. Soc. Trans., vol. 17, pp. 947-949 (19898).

Chung, L.A. et al., "Fluorescence Studies of the Secondary Structure and Orientation of a Model Ion Channel Peptide in Phospholipid Vesicles," Biochemistry, vol. 31, pp. 6608-6616 (1992).

Cornut et al., "The Amphipathic $\alpha$-Helix Concept: Application to the De Novo Design of Ideally Amphipathic Leu, Lys Peptides with Hemolytic Activity Higher than That of Melittin," FEBS (Federation of European Biochemical Societies) Letters, vol. 349, pp. 29-33 (1994).

(Continued)

Primary Examiner—Anish Gupta
(74) Attorney, Agent, or Firm—John H. Runnels; Bonnie J. Davis

(57) ABSTRACT

"Minimalist" antimicrobial peptides are disclosed based on 50 to 80% $\alpha,\alpha$-dialkylated amino acids. The peptides are short, cationic, amphipathic, and possess a high helix propensity. Polar $\alpha,\alpha$-dialkylated amino acids are also disclosed. These peptides are easy and inexpensive to synthesize via solid-phase techniques. The peptides exhibit in vitro anti-bacterial properties at concentrations that are not lethal to normal mammalian cells. The peptides exhibit in vivo bioactivity against intracellular pathogens.

40 Claims, 2 Drawing Sheets

OTHER PUBLICATIONS

DeGrado, W.F. et al., "Conformationally Constrained α-Helical Peptide Models for Protein Ion Channels," Biopolymers, vol. 29, pp. 205-213 (1990).

Epand et al., "Mechanisms for the Modulation of Membrane Bilayer Properties by Amphipathic Helical Peptides," Biopolymers (Peptide Science) vol. 37, pp. 319-338 (1995)).

Himelsbech et al., "Preparation of Amide Group-Containing Compounds as Antithrombotics," Chemical Abstracts, vol. 123, No. 256522 (1955).

Iwata, T. et al., "Design and Synthesis of Amphipathic 310-Helical Peptides and Their Interactions with Phospholipid Bilayers and Ion Channel," J. Bio. Chem., vol. 269, pp. 4928-4933 (1994).

Jacobsen, P. et al., "Potential GABA Uptake Inhibitorrs, Synthesis and Relative Stereochemistry of Some Aminopiperidinecarboxylic Acids," Acta Chem. Scand., B 34, pp. 319-326 (1980).

Javadpour et al., "*De Novo* Antimicrobial Peptides with Low Mammalian Cell Toxicity," Journal of Medicinal Chemistry, vol. 39, pp. 3107-3113 (1996).

Jaynes et al., "*In vitro* Cytocidal Effect of Lytic Peptides in Several Transformed Mammalian Cell Lines," Peptide Research, vol. 2, pp. 157-160 (1989).

Karle et al., "Structural Characteristics of α-Helical Peptide Molecules Containing Aib Residues," Biochemistry, vol. 29, No. 29, pp. 6747-6756 (1990).

Kono et al., "pH Dependent Interaction of Amphiphilic Polypeptide Poly(LYS-AIB-LEU-AIB) with Lipid Bilayer Membrane," Biochemistry, vol. 29, pp. 3631-3637 (1990).

Lee et al., "Relationship Between Antimicrobial Activity and Amphipathic Property of Basic Model Peptides," Biochimica et Biophysica Acta, vol. 862, pp. 211-219 (1986).

Maloy, W. et al., "Structure-Activity Studies on Magainins and Other Host Defense Peptides," Biopolymers, vol. 37, pp. 105-122 (1995).

McLean, L.R. et al., "Minimal Peptide Length for Interaction of Amphipathic α-Helical Peptides with Phosphatidylcholine Liposomes," Biochemistry, vol. 30, pp. 31-37 (1991).

Nagaraj et al., "Alamethicin, a Transmembrane Chemical," Accounts of Chemical Research, vol. 14, pp. 356-362 (1981).

O'Shea, E.K. et al., "X-ray Structure of the GCN4 Leucine Zipper, a Two-Stranded, Parallel Coiled Coil," Science, vol. 254, pp. 539-544 (1991).

Patel, "Peptide Drug Delivery," Biochem. Soc. Trans., vol. 17, p. 931 (1989).

Saberwal et al., "Cell-Lytic and Antibacterial Peptides that Act by Perturbing the Barrier Function of Membranes: Facets of their Conformational Features, Structure-Function Correlations and Membrane-Perturbing Abilities," Biochimica et Biophysica Acta, vol. 1197, pp. 109-131 (1994).

Sarkarelos et al., "Sequential Oligopeptides as Carriers of Multiple Antigenic Peptides: Synthesis-Structure Properties," Pept. 1994, Proc. Eur. Pept. Symp., 23$^{rd}$ (1995), pp. 817-818, Meeting Date 1994.

Sakarellos-Daitsiotis, M. et al., "A new helicoid-type sequential oligopeptide carrier (SOC(n)) for developing potent antigens and immunogens," Vaccine, vol. 18, pp. 302-310 (1999).

Sakarellos-Daitsiotis, M. et al., "Peptide carriers: A helicoid-type sequential oligopeptide carrier (SOC(n)) for multiple anchoring of antigenic/immunogenic peptides," Methods, vol. 19, pp. 133-141 (1999).

Wysong et al., "4-Aminopiperdine-4-carboxylic Acid: A Cyclic α,α-Disubstituted Amino Acid for Preparation of Water-Soluble Highly Helical Peptides," Journal of Organic Chemistry, vol. 61, No. 22, pp. 7650-7651 (1996).

Yokum et al., "Solvent Effects on the $3_{10}$-/α-Helix Equilibrium in Short Amphipathic Peptides Rich in α,α-Disubstituted Amino Acids," Journal of the American Chemical Society, vol. 119, pp. 1167-1168 (1997).

Yokum et al., "Antimicrobial α,α-Dialkylated Amino Acid Rich Peptides with *In-Vivo* Activity against an intracellular Pathogen," Journal of Medicinal Chemistry, vol. 39, No. 19, pp. 3603-3605 (1996).

Zhao et al., "Amphiphilic Alpha Helical Structure in Water Stabilized by Dioctadecyl Chain," J. Chem. Soc. Perkin Trans. 2, vol. 12, pp. 2243-2248 (1995).

Zhou, N.E. et al., "Synthetic Model Proteins: The Relative Contribution of Leucine Residues at the Nonequivalent Positions of the 3-4 Hydrophobic Repeat to the Stability of the Two-Stranded α-Helical Coiled-Coil," Biochemistry, vol. 31, pp. 5739-5746 (1992).

Zier, A. et al., "Polyethylene Glycol Bound Benzyl- and Fluorenyl Derivatives as Solubilizing Side-Chain Protecting Groups in Peptide Synthesis," Tetrahedron Letters, vol. 35, pp. 1039-1042 (1994).

* cited by examiner

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (D) OTHER INFORMATION: /note= "Amidated at C-terminus;"

(x) PUBLICATION INFORMATION:
        (A) AUTHORS: Yokum, T. S.
            Elzer, Philip H.
            McLaughlin, Mark L.
        (B) TITLE: Antimicrobial alpha, alpha-dialkylated Amino
            Acid Rich Peptides with in-Vivo Activity against
            an Intracellular Pathogen
        (C) JOURNAL: Journal of Medicinal Chemistry
        (D) VOLUME: 39
        (E) ISSUE: 19
        (F) PAGES: 3603-3605
        (G) DATE: 13-Sept-1996
        (K) RELEVANT RESIDUES IN SEQ ID NO:1: FROM 1 TO 14

(xi) SEQUENCE DESCRIPTION: SEQ ID NO:1:

Lys Ala Ala Lys Lys Ala Ala Lys Ala Ala Lys Lys Ala Ala
1               5                   10

(2) INFORMATION FOR SEQ ID NO:2:

(i) SEQUENCE CHARACTERISTICS:
        (A) LENGTH: 14 amino acids
        (B) TYPE: amino acid
        (D) TOPOLOGY: linear (ii) MOLECULE TYPE: peptide (ix) FEATURE:
        (A) NAME/KEY: Peptide
        (B) LOCATION: 14
        (D) OTHER INFORMATION: /note= "Amidated at C-terminus;

```
               Xaa
               is Aib;"

(x) PUBLICATION INFORMATION:
           (A) AUTHORS: Yokum, T. S.
               Elzer, Philip H.
               McLaughlin, Mark L.
           (B) TITLE: Antimicrobial alpha, alpha-dialkylated Amino
               Acid Rich Peptides with in-vivo Activity against
               an Intracellular Pathogen
           (C) JOURNAL: Journal of Medicinal Chemistry
           (D) VOLUME: 13-Sep19
           (E) ISSUE: 19
           (F) PAGES: 3603-3605
           (G) DATE: 13-Sept-1996
           (K) RELEVANT RESIDUES IN SEQ ID NO:2: FROM 1 TO 14

(xi) SEQUENCE DESCRIPTION: SEQ ID NO:2:

Lys Xaa Xaa Lys Lys Xaa Xaa Lys Xaa Xaa Lys Lys Xaa Xaa
 1               5                  10

(2) INFORMATION FOR SEQ ID NO:3:

(i) SEQUENCE CHARACTERISTICS:
           (A) LENGTH: 11 amino acids
           (B) TYPE: amino acid
           (D) TOPOLOGY: linear (ii) MOLECULE TYPE: peptide (ix) FEATURE:
           (D) OTHER INFORMATION: /note= "Amidated at C-terminus;
               Xaa
               is Aib;"

(x) PUBLICATION INFORMATION:
           (A) AUTHORS: Yokum, T. S.
               Elzer, Philip H.
               McLaughlin, Mark L.
           (B) TITLE: Antimicrobial alpha, alpha-Dialkylated Amino
               Acid Rich Peptides with in-Vivo Activity against
               an Intracellular Pathogen
           (C) JOURNAL: Journal of Medicinal Chemistry
           (D) VOLUME: 39
           (E) ISSUE: 19
           (F) PAGES: 3603-3605
           (G) DATE: 13-Sept-1996
           (K) RELEVANT RESIDUES IN SEQ ID NO:3: FROM 1 TO 11

(xi) SEQUENCE DESCRIPTION: SEQ ID NO:3:

Lys Lys Xaa Xaa Lys Xaa Xaa Lys Lys Xaa Xaa
 1               5                  10

(2) INFORMATION FOR SEQ ID NO:4:

(i) SEQUENCE CHARACTERISTICS:
           (A) LENGTH: 14 amino acids
           (B) TYPE: amino acid
           (D) TOPOLOGY: linear (ii) MOLECULE TYPE: peptide (ix) FEATURE:
           (D) OTHER INFORMATION: /note= "Amidated at C-terminus;
               Xaa
               is 1-amino-1-cyclohexanecarboxylic acid;"

(x) PUBLICATION INFORMATION:
           (A) AUTHORS: Yokum, T. S.
               Elzer, Philip H.
               McLaughlin, Mark L.
           (B) TITLE: Antimicrobial alpha, alpha-Dialkylated Amino
               Acid Rich Peptides with in-Vivo Activity against
               an Intracellular Pathogen
           (C) JOURNAL: Journal of Medicinal Chemistry
```

```
        (D) VOLUME: 39
        (E) ISSUE: 19
        (F) PAGES: 3603-3605
        (G) DATE: 13-Sept-1996
        (K) RELEVANT RESIDUES IN SEQ ID NO:4: FROM 1 TO 14

(xi) SEQUENCE DESCRIPTION: SEQ ID NO:4:

Lys Xaa Xaa Lys Lys Xaa Xaa Lys Xaa Xaa Lys Lys Xaa Xaa
1               5                   10

(2) INFORMATION FOR SEQ ID NO:5:

(i) SEQUENCE CHARACTERISTICS:
        (A) LENGTH: 11 amino acids
        (B) TYPE: amino acid
        (D) TOPOLOGY: linear (ii) MOLECULE TYPE: peptide (ix) FEATURE:
        (D) OTHER INFORMATION: /note= "Amidated at C-terminus;
            Xaa
            is 1-amino-1-cyclohexanecarboxylic acid;"

(x) PUBLICATION INFORMATION:
        (A) AUTHORS: Yokum, T. S.
            Elzer, Philip H.
            McLaughlin, Mark L.
        (B) TITLE: Antimicrobial alpha, alpha-Dialkylated Amino
            Acid Rich Peptides with in-Vivo Activity against
            an Intracellular Pathogen
        (C) JOURNAL: Journal of Medicinal Chemistry
        (D) VOLUME: 39
        (E) ISSUE: 19
        (F) PAGES: 3603-3606
        (G) DATE: 13-Sept-1996
        (K) RELEVANT RESIDUES IN SEQ ID NO:5: FROM 1 TO 11

(xi) SEQUENCE DESCRIPTION: SEQ ID NO:5:

Lys Lys Xaa Xaa Lys Xaa Xaa Lys Lys Xaa Xaa
1               5                   10

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: linear (ii) MOLECULE TYPE: peptide (ix) FEATURE:
        (D) OTHER INFORMATION: /note= "Amidated at C-terminus;
            Xaa
            is 1-amino-1-cyclohexanecarboxylic acid;"

(x) PUBLICATION INFORMATION:
        (A) AUTHORS: Yokum, T. S.
            Elzer, Philip H.
            McLaughlin, Mark L.
        (B) TITLE: Antimicrobial alpha, alpha-Dialkylated Amino
            Acid Rich Peptides with in-Vivo Activity against
            an Intracellular Pathogen
        (C) JOURNAL: Journal of Medicinal Chemistry
        (D) VOLUME: 39
        (E) ISSUE: 19
        (F) PAGES: 3603-3605
        (G) DATE: 13-Sept-1996
        (K) RELEVANT RESIDUES IN SEQ ID NO:6: FROM 1 TO 13

(xi) SEQUENCE DESCRIPTION: SEQ ID NO:6:

Lys Xaa Xaa Lys Lys Xaa Xaa Lys Xaa Xaa Lys Lys Xaa
1               5                   10
```

(2) INFORMATION FOR SEQ ID NO:7:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Amidated at C-terminus;
            Xaa
            is 1-amino-1-cyclohexanecarboxylic acid;"

(x) PUBLICATION INFORMATION:
        (A) AUTHORS: Yokum, T. S.
            Elzer, Philip H.
            McLaughlin, Mark L.
        (B) TITLE: Antimicrobial alpha, alpha-Dialkylated Amino
            Acid Rich Peptides with in-Vivo Activity against
            an Intracellular Pathogen
        (C) JOURNAL: Journal of Medicinal Chemistry
        (D) VOLUME: 39
        (E) ISSUE: 19
        (F) PAGES: 3603-3605
        (G) DATE: 13-Sept-1996
        (K) RELEVANT RESIDUES IN SEQ ID NO:7: FROM 1 TO 10

(xi) SEQUENCE DESCRIPTION: SEQ ID NO:7:

```
Lys Lys Xaa Xaa Lys Xaa Xaa Lys Lys Xaa
1               5                   10
```

(2) INFORMATION FOR SEQ ID NO:8:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Amidated at C-terminus;
            Xaa
            at 1, 2, 5, 6, 9 and 10 is Aib; Xaa at 3 and 7
            is
            4-aminopiperidine-4-carboxylic acid;"

(x) PUBLICATION INFORMATION:
        (A) AUTHORS: Yokum, T. S.
            Elzer, Philip H.
            McLaughlin, Mark L.
        (B) TITLE: Antimicrobial alpha, alpha-Dialkylated Amino
            Acid Rich Peptides with in-Vivo Activity against
            an Intracellular Pathogen
        (C) JOURNAL: Journal of Medicinal Chemistry
        (D) VOLUME: 39
        (E) ISSUE: 19
        (F) PAGES: 3603-3605
        (G) DATE: 13-Sept-1996
        (K) RELEVANT RESIDUES IN SEQ ID NO:8: FROM 1 TO 10

(x) PUBLICATION INFORMATION:
        (A) AUTHORS: Yokum, T. S.
            Gauthier, Ted J.
            Hammer, Robert P.
            McLaughlin, Mark L.
        (B) TITLE: Solvent Effects on the 310/alpha-Helix
            Equilibrium in Short Amphipathic Peptides Rich
            in
            alpha,alpha-Disubstituted Amino Acids
        (C) JOURNAL: J. Am. Chem. Soc.
        (G) DATE: 1997
        (K) RELEVANT RESIDUES IN SEQ ID NO:8: FROM 1 TO 10

(xi) SEQUENCE DESCRIPTION: SEQ ID NO:8:

```
Xaa Xaa Xaa Lys Xaa Xaa Xaa Lys Xaa Xaa
1               5                   10
```

(2) INFORMATION FOR SEQ ID NO:9:

(i) SEQUENCE CHARACTERISTICS:
        (A) LENGTH: 10 amino acids
        (B) TYPE: amino acid
        (D) TOPOLOGY: linear (ii) MOLECULE TYPE: peptide (ix) FEATURE:
        (D) OTHER INFORMATION: /note= "Amidated at C-terminus;
            Xaa
            at 1 and 10 is 4-aminopiperidine-4-carboxylic
            acid; Xaa at 2, 3, 5, 6, 8, and 9 is Aib;"

(x) PUBLICATION INFORMATION:
        (A) AUTHORS: Yokum, T. S.
            Gauthier, Ted J.
            Hammer, Robert P.
            McLaughlin, Mark L.
        (B) TITLE: Solvent Effects on the 310/alpha-Helix
            Equilibrium in Short Amphipathic Peptides Rich
            in
            alpha,alpha-Disubstituted Amino Acids
        (C) JOURNAL: J. Am. Chem. Soc.
        (G) DATE: 1997
        (K) RELEVANT RESIDUES IN SEQ ID NO:9: FROM 1 TO 10

(xi) SEQUENCE DESCRIPTION: SEQ ID NO:9:

```
Xaa Xaa Xaa Lys Xaa Xaa Lys Xaa Xaa Xaa
1               5                   10
```

(2) INFORMATION FOR SEQ ID NO:10:

(i) SEQUENCE CHARACTERISTICS:
        (A) LENGTH: 18 amino acids
        (B) TYPE: amino acid
        (D) TOPOLOGY: linear (ii) MOLECULE TYPE: peptide (x) PUBLICATION INFORMATION:
        (A) AUTHORS: Blondelle, Sylvie E.
            Houghten, Richard A.
        (B) TITLE: Design of Model Amphipathic Peptides Having
            Potent Antimicrobial Activities
        (C) JOURNAL: Biochemistry
        (D) VOLUME: 31
        (F) PAGES: 12688-12694
        (G) DATE: 1992
        (K) RELEVANT RESIDUES IN SEQ ID NO:10: FROM 1 TO 18

(xi) SEQUENCE DESCRIPTION: SEQ ID NO:10:

```
Lys Leu Lys Leu Leu Lys Lys Leu Leu Lys Lys Leu Lys Lys Leu Leu
1               5                   10                  15
Lys Leu
```

SHORT AMPHIPATHIC PEPTIDES WITH ACTIVITY AGAINST BACTERIA AND INTRACELLULAR PATHOGENS

This is a continuation of copending application Ser. No. 09/019,490, filed Feb. 5, 1998 now U.S. Pat. No. 6,566,334, which claims the benefit of the Feb. 6, 1997 filing date of provisional application 60/183,014 under 35 U.S.C. § 119 (e).

The development of this invention was partially funded by the Government under grant NSF/LEQSF (1992–96)-ADP-01 awarded by the National Science Foundation. The Government may have certain rights in this invention.

This invention pertains to amphipathic peptides having activity against bacteria and intracellular pathogens.

Bacterial resistance has hampered antibiotic therapy since the discovery of penicillin. The efficacy of current antibiotics is declining at an alarming rate due to the increase of multi-drug resistant bacteria. The lack of effectiveness arises from current antibiotics' reliance on few unique mechanisms of action. There is an unfilled need for new drugs with novel mechanisms of action upon bacterial infections.

Intracellular pathogens are especially difficult to control because they are sequestered within host cells. For example, Brucella abortus is an intracellular pathogen that lives and replicates in host macrophages. The ability to survive in macrophages allows Brucella to quickly establish a chronic infection. Treatment of chronic brucellosis is difficult because the sequestered bacteria are not exposed to the body's immune response system: complement cascade, neutrophils, Brucella-specific antibodies, and the host's cellular immune response. See Araya et al., "Temporal Development or Protective Cell-Mediated and Humoral Immunity in BALB/c Mice Infected with Brucella abortus," Journal of Immunology, vol. 53, pp. 3330–3337 (1989).

Brucella are short, non-motile, non-sporulating, non-encapsulated, Gram-negative aerobic rods. Brucella are important veterinary pathogens. The bacteria localize in reproductive organs, mammary glands, supramammary lymph nodes, and other reticuloendothelial tissues, leading to abortion and infertility.

The zoonotic bacterial disease brucellosis has a significant impact on human health worldwide. In humans, Brucella infection results in a chronic debilitating disease known as undulant fever. Humans are exposed through direct contact with infected animals or infected animal products. In the United States, human brucellosis is an occupational hazard for veterinarians, abattoir (slaughterhouse) workers, animal handlers, and laboratory workers. Due to the highly infectious nature of the Brucella species via aerosolization, several members of the genus are candidates for biological weapons, placing military personnel at risk for infections.

Human brucellosis is characterized by malaise, fever, anorexia, muscular weakness, arthritis, and dementia. Cardiac and neurologic disorders may occur and, if untreated, may result in a mortality rate as high as 10%. Lengthy antibiotic therapy with one or multiple drugs for up to 30–45 days is required to treat brucellosis, but relapses of infection often occur after treatment is stopped. Unfortunately, antibiotic therapy does not relieve the symptoms of malaise, depression, and occasional severe dementia associated with the disease. Currently there are no vaccines available for humans; the live vaccines used in the eradication of animal brucellosis are virulent for man.

The BALB/c mouse model has been widely used for Brucella pathogenesis and vaccine efficacy studies. Inoculation of mice with virulent Brucella results in colonization of the liver and spleen. The immune response of mice to Brucella is similar to that observed in the natural hosts and humans. Cell-mediated immune (CMI) responses that aid in the clearance of infections have been defined in the murine model (Araya, et al., 1989). In general, vaccine strains that induce protective immunity in the natural hosts demonstrate abbreviated colonization profiles and also confer protection in mice.

Another example of an intracellular pathogen is Mycobacterium tuberculosis, an acid-fast Gram-positive bacterium that is the main cause of tuberculosis in humans. Tuberculosis is the leading cause of human deaths due to an infectious organism; estimates are that a third of the world's population is currently infected. Approximately 3 million people die from tuberculosis annually, and it is expected that this number will steadily increase over the next decade as drug resistant strains proliferate.

Organisms have many defense mechanisms against invasion by pathogens, including the cellular release of defense peptides. Some defense peptides perturb the barrier function of the membrane of either the invading pathogen or of infected host cells. Although the mechanism is not completely understood, it is thought that the defense peptide forms a transmembrane channel that allows irregular ion transport across the membrane, resulting in cell lysis or death due to a loss of osmotic integrity. See Saberwal et al., "Cell-Lytic and Antibacterial Peptides that Act by Perturbing the Barrier Function of Membranes: Facets of their Conformational Features, Structure-Function Correlations and Membrane-Perturbing Abilities," Biochimica et Biophysica Acta, vol. 1197, pp. 109–131 (1994).

Many antimicrobial peptides selectively inhibit and kill bacterial cells while maintaining low cytotoxicity for normal mammalian cells. The selectivity for pathogens has been attributed to a difference between bacterial and mammalian cell membranes. The exterior membranes of bacteria are negatively charged, whereas mammalian cell exterior membranes are generally neutral. Antimicrobial peptides are positively charged and therefore may preferentially bind to bacterial membranes. The cholesterol in mammalian cell membranes has also been suggested as the basis for the selectivity of antimicrobial peptides. See Maloy et al., "Structure-Activity Studies on Magainins and Other Host Defense Peptides," Biopolymers (Peptide Science), vol. 37, 105–122 (1995). Membrane disruption by the antimicrobial peptides could be inhibited by cholesterol. Finally the lower membrane potential across mammalian cells, or some combination of the above factors, could be responsible for the observed selectivity of the antimicrobial peptides between bacteria and normal mammalian cells.

The specificity of various antimicrobial peptides differs. For example, melittin, a component of honeybee venom, is not selective. The minimum bactericidal concentration of melittin also damages normal mammalian cells. By contrast, the naturally occurring magainins and cecropins exhibit substantial bactericidal activity at concentrations that are not lethal to normal mammalian cells. It has been found that sequence homology is not a prerequisite for biological activity. (Saberwal et al., 1994) Many natural antimicrobial peptides of widely varying sequences have been isolated. One consistent structural feature is the presence of an amphipathic helical domain. Synthetic analogs of native peptides with amino acid substitutions expected to enhance amphipathicity and helicity have shown increased biological activity. However, most analogs with increased antimicrobial activity unfortunately also show increased cytotoxicity against normal mammalian cells. Notable exceptions are the melittin-cecropin hybrids, which are more bacteriostatic than cecropins and less cytotoxic than melittin. Melittin, a 26-residue peptide, is cytotoxic and has broad spectrum antimicrobial activity at micromolar concentrations. There are a number of other natural amphipathic peptides that are much less cytotoxic than melittin, but that have comparable broad spectrum antimicrobial activity. Magainins and cecropins exhibit bacteriostatic and bactericidal activity at concentrations that are not cytotoxic toward normal mammalian cells. These peptides are unstructured in dilute aqueous solution, but become helical in amphipathic media such as micelles, synthetic bilayers, and cell membranes.

Some defense peptides have been reported to selectively attack host cells infected with an intracellular pathogen, while not affecting normal mammalian cells. See Barr et al., "Activity of Lytic Peptides Against Intracellular *Trypanosoma cruzi* Amastigotes in vitro and Parasitemias in Mice," Journal of Parasitology, vol. 81, no. 6, pp. 974–978 (1995). Such selectivity has not been previously reported for *Brucella* infection. There have been no previous studies on in vivo activity of a peptide against an intracellular pathogen. The mechanism for peptide selectivity against host cells infected with a pathogen is unknown. Three possibilities include the following: (1) the peptide has greater binding affinity to infected host cells; (2) the peptide binds to both infected and normal cells, but the normal cell is able to repair the membrane; and (3) the membrane of the infected cell is inherently defective, so the binding of the peptide causes cell death. See Jaynes et al., "In vitro Cytocidal Effect of Lytic Peptides in Several Transformed Mammalian Cell Lines," Peptide Research, vol. 2, pp. 157–160 (1989).

Antimicrobial peptides generally have random coil conformations in dilute aqueous solutions. However, high levels of helicity can be induced by helix-promoting organic solvents and amphipathic media such as micelles, synthetic bilayers, and cell membranes. When helicity is induced, the polar and nonpolar amino acid residues are aligned into an amphipathic helix. The amphipathic $\alpha$-helix is a common structural motif of many proteins and biologically active peptides. An amphipathic peptide or protein is one in which the hydrophobic amino acid residues are predominantly on one side of the helix looking down the helical axis, while the hydrophilic amino acid residues are predominantly on the opposite side, resulting in a peptide or protein that is predominantly hydrophobic on one face, and predominantly hydrophilic on the opposite face. Amphipathic helical domains are found in membrane recognition sites, such as specific ion channel proteins, signal peptides, and antimicrobial and venom peptides. The interaction of amphipathic peptides with membranes depends at least in part on the relative sizes of the hydrophobic and hydrophilic faces and the charge density of the hydrophilic face. Natural antimicrobial peptides generally have an equivalent number of polar and nonpolar residues within the amphipathic domains, and enough basic residues to give the peptide an overall positive charge at neutral pH.

Antimicrobial peptides based upon an amphipathic $\alpha$-helix have been known for decades (Saberwal et al., 1994; Epand et al., "Mechanisms for the Modulation of Membrane Bilayer Properties by Amphipathic Helical Peptides," Biopolymers (Peptide Science) vol. 37, pp. 319–338 (1995)). The mechanism of action of this class of peptides, typified by cecropins from the *Hyalophora* moth and magainins from the African clawed frog, *Xenopus laevis*, is still a matter of controversy (Epand, et al., 1995). There is abundant evidence that these peptides disrupt the barrier function of the membranes of susceptible cells.

Many natural peptides of this class have now been isolated from taxa ranging from bacteria to mammals. De novo peptides having $\alpha$-helical domains likely to form amphipathic $\alpha$-helices have been synthesized and shown to have in vitro antimicrobial activity against a broad spectrum of Gram-positive and Gram-negative bacteria. See Javadpour et al., "De Novo Antimicrobial Peptides with Low Mammalian Cell Toxicity," Journal of Medicinal Chemistry, vol. 39, pp. 3107–3113 (1996). Several examples demonstrate that chiral recognition is not required, as all L-peptides or all D-peptides have the same bioactivity in vitro. In addition to having an amphipathic $\alpha$-helix, there is apparently a need for at least some overall positive charge for the peptide to be active. Essentially all the natural peptides have at least one overall positive charge, but these peptides also usually have some uncharged polar and even some negatively charged amino acids that help to form the polar face of the amphipathic domain.

Careful studies of the structure and orientation of the peptides show that peptides of this class bind as $\alpha$-helices, with the nonpolar face of the peptides embedded in the phospholipid membrane, lying perpendicular to the fatty acid chains of the phospholipids (Epand et al., 1995). This conformation is called "peptide rafting" since the hydrophobic faces of the peptides partially sink into the phospholipid surface and may become loosely bound together, like the logs of a raft, causing cell membrane disruption. An alternative explanation is that while the vast majority of peptides lie perpendicular to phospholipid bilayer, one or a few peptide aggregates could self-assemble as nonspecific transmembrane pores. (Epand et al., 1995). A transmembrane channel model suggests a minimum $\alpha$-helix length would be required to span the hydrophobic core of the phospholipid bilayer. The average hydrophobic core of a bilayer at equilibrium is about 40 Å. Spanning this length would require a peptide of about 20 residues.

Synthetic analogs of several naturally occurring cytotoxic peptides have previously been synthesized, but in the past it has been laborious and expensive to synthesize these synthetic peptides in large quantities. There is a continuing need for synthetic antimicrobial peptides that are easy to synthesize, and that exhibit antibacterial activity or activity against intracellular pathogens at concentrations that are not lethal to normal mammalian cells.

One of the earliest designed peptides was a melittin analog with a simplified N-terminus and the native C-terminal segment that had hemolytic activity comparable to that of melittin. Another designed amphipathic $\alpha$-helical peptide had 12 to 22 residues, composed of 2:1 Leu and Lys residues, with a narrow polar face. The peptides with 15, 20 and 22 residues showed over 10-fold higher hemolytic activity than melittin. See Cornut et al., "The Amphipathic $\alpha$-Helix Concept: Application to the De Novo Design of Ideally Amphipathic Leu, Lys Peptides with Hemolytic Activity Higher than That of Melittin," FEBS (Federation of European Biochemical Societies) Letters, vol. 349, pp. 29–33 (1994). D-Melittin, D-magainin, and D-cecropin derivatives have biological activities that are essentially the same as those of the native L-peptides. De novo peptides that use the amphipathic helix as a starting point have been synthesized and have exhibited bacteriostatic and cytotoxic activities similar to those of the native peptides. See Lee et al., "Relationship Between Antimicrobial Activity and Amphipathic Property of Basic Model Peptides," Biochimica et Biophysica Acta, vol. 862, pp. 211–219 (1986); and Blondelle et al., "Design of Model Amphipathic Peptides Having Potent Antimicrobial Activities, Biochemistry, vol. 31, pp. 12688–12694 (1992). Structure-activity studies have shown a relationship between antibacterial activity, peptide length, and the proportion of positively-charged and hydrophobic residues. See Bessalle et al., "Structure-Function Studies of Amphiphilic Antibacterial Peptides," Journal of Medicinal Chemistry, vol. 36, pp. 1203–1209 (1993).

One class of natural antimicrobial peptides, peptaibols, have several α-aminoisobutyric acid (Aib) residues, are acetylated on the N-terminus, and have an amino alcohol at the C-terminus. See Benedetti et al., "Peptaibol Antibiotics: A Study on the Helical Structure of the 2–9 Sequence of Emerimicins III and IV," Proceedings of the National Academy of Sciences, vol. 79, pp. 7951–7954 (1982). The Aib residue is a nonpolar α,α-dialkylated amino acid (an α-amino acid residue that is dialkylated at the α carbon), which is believed to stabilize a helical structure. For example, alamethicin, a 20-residue peptide, is rich in Aib residues (up to 50%) and exists primarily as either an α- or $3_{10}$-helix. (In an α helix the NH of the i+4 residue is hydrogen bonded to the CO of residue i (5→1), whereas in the $3_{10}$ helix the i+3 NH group participates in a 4→1 hydrogen bond.) This peptide is known to form membrane channels. See Nagaraj et al., "Alamethicin, a Transmembrane Channel," Accounts of Chemical Research, vol. 14, pp. 356–362 (1981). In addition, peptides with several α,α-dialkylated amino acids throughout the sequence are resistant to enzymatic hydrolysis, especially by trypsin, which enhances in vivo activity.

The nonpolar α,α-dialkylated amino acids (or hydrophobic α,α-dialkylated amino acids), especially Aib, have been incorporated into peptides to control the secondary structure of the peptide. See Karle et al., "Structural Characteristics of α-Helical Peptide Molecules Containing Aib Residues," Biochemistry, vol. 29, no. 29, pp. 6747–6756 (1990).

One polar α,α-dialkylated amino acid (i.e., a substituted, hydrophilic α,α-dialkylated amino acid) that has been synthesized is 4-aminopiperidine-4-carboxylic acid (Api). See Jacobsen et al., "Potential GABA Uptake Inhibitors. Synthesis and Relative Stereochemistry of Some Aminopiperidinecarboxylic acids," Acta Chemica Scandinavica B, vol. 34, pp. 319–326 (1980). There is no known prior report incorporating a polar α,α-dialkylated amino acid into a peptide. There is no known prior report of the preparation of a protected derivative of a polar α,α-dialkylated amino acid that would be suitable for peptide synthesis.

Peptides with α,α-dialkylated amino acids are sterically constrained because of the disubstitution about the α-carbon. There are two potential helical conformations for peptides containing α,α-dialkylated amino acids: $3_{10}$ or α-helical. In larger peptides, increasing the number of α,α-dialkylated amino acids tends to promote specific helical conformation. The more α,α-dialkylated amino acids that are used in a peptide the greater the steric constraint toward helicity. For Aib containing peptides, it appears that 50% α,α-dialkylated amino acids induce $3_{10}$-helical conformation in peptides of 10 residues. See Basu et al., "Conformational Preferences of Oligopeptides Rich in α-Aminoisobutyric Acid. I. Observation of a $3_{10}$/α-Helical Transition upon Sequence Permutation," Biopolymers, vol. 31, pp. 1763–1774 (1991). Additionally, 24-residue peptides with a lysine or arginine at every third residue have been reported to be an amphipathic $3_{10}$-helix. However, this peptide had no antimicrobial activity. See Iwata et al., "Design and Synthesis of Amphipathic $3_{10}$-Helical Peptides and Their Interactions with Phospholipid Bilayers and Ion Channel Formation," Journal of Biological Chemistry, vol. 269, no. 7, pp. 4928–4933 (1994).

The overall length of the peptide plays a role in determining the conformation, in conjunction with the number of α,α-dialkylated amino acids. The effect of a single α,α-dialkylated amino acid in influencing the secondary structure is greatest in small peptides; as the length of peptide chain increases the effect diminishes. Thus it is necessary to increase the percentage of α,α-dialkylated amino acids in order to promote the $3_{10}$ helical conformation (Bendetti et al., 1982).

S. E. Blondelle et al., "Design of Model Amphipathic Peptides Having Potent Antimicrobial Activities," Biochemistry, vol. 31, pp. 12688–12694 (1992) reports that the sequence LKLLKKLLKKLKKLLKKL (SEQ ID NO. 10) adopts an α-helical conformation, and that the peptide has activity against both Gram-positive and Gram-negative bacteria. The activities of certain analogs having various substitutions, omissions, and lengths are also discussed.

W. F. DeGrado et al., "Conformationally Constrained α-Helical Peptide Models for Protein Ion Channels," Biopolymers, vol. 29, pp. 205–213 (1990) discusses amphiphilic α-helical models for ion channels formed from various peptides composed of only Leu and Ser residues, or a modification of such a peptide incorporating α-aminoisobutyric acid.

We have invented novel "minimalist" antimicrobial peptides, based on 50 to 80% α,α-dialkylated amino acids, that may be readily synthesized on a large scale, for example by standard Fmoc solid-phase synthesis techniques. The novel peptides are short, cationic, amphipathic, and form a helix. We have also invented new polar α,α-dialkylated amino acids and a process to produce protected derivatives of polar α,α-dialkylated amino acids for incorporation into peptides. These synthetic peptides are easy and inexpensive to synthesize via solid-phase techniques. The present invention has found peptides as short as 10 residues that exhibit antibacterial activity at concentrations that are not lethal to normal mammalian cells, and that also exhibit bioactivity against intracellular pathogens. These synthetic peptides with a high percentage of α,α-dialkylated amino acids were also found to be resistant to tryptic digestion.

Figure 1:
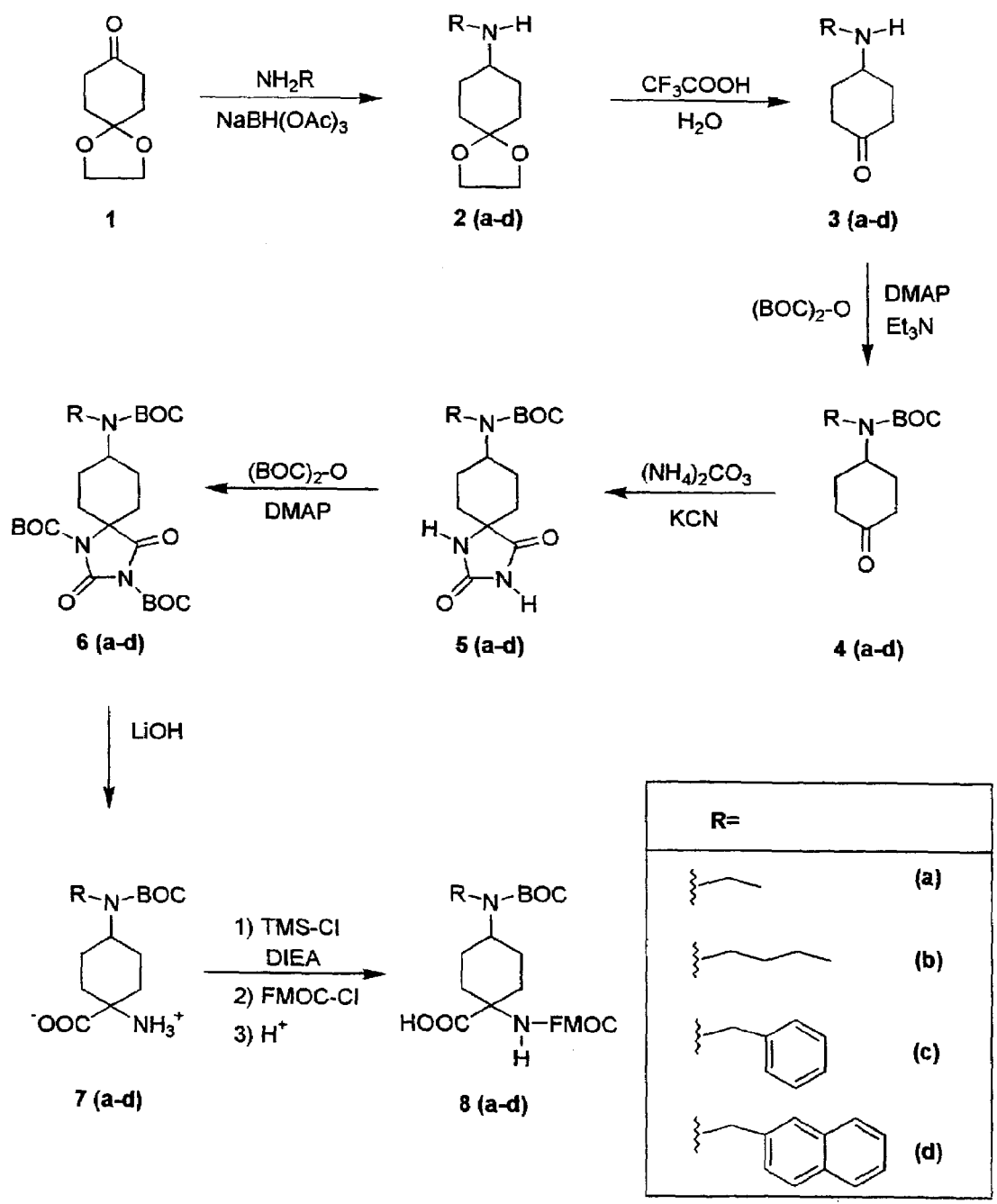
FIG. 1 illustrates a synthetic pathway for four positively charged α,α-dialkylated amino acids with corresponding R groups (a–d).

The novel peptides, which have in vivo antimicrobial activity, are designed to form amphipathic α-helices or $3_{10}$-helices, and comprise several xenobiotic amino acids, conferring a higher degree of protease resistance than is found in native peptides. α,α-Dialkylated amino acids have been used to induce helical secondary structure. The induced helicity of these peptides has allowed the peptides to be significantly shortened while retaining biological activity. The peptides designed to form $3_{10}$-helices did so in sodium dodecylsulfate (SDS) micelles, and the peptides designed to form α-helices in SDS micelles did so, both as determined by CD spectroscopy. In addition, the $3_{10}$-helix peptides undergo a transition from an α-helix to a $3_{10}$-helix as the concentration of organic solvent in the surrounding solution increases.

The peptides designed to have primarily an α-helix secondary structure comprise 7 to 20 residues, preferably 8 to 14 residues. The peptides contain 25 to 100% residues that are α,α-dialkylated amino acids. The peptides also contain 25 to 50% polar amino acid residues such that the peptide has an overall positive charge under physiological conditions, and 25 to 75% nonpolar α,α-dialkylated amino acid residues. The nonpolar residues and the polar residues are distributed within the peptide such that when the peptide forms an α-helix under physiological conditions, the nonpolar residues lie on one face of the α-helix and the polar residues lie on the opposite face of the α-helix, making the peptide amphipathic. Without wishing to be bound by this theory, it is believed that an α-helix of 8 residues is just long enough to cause membrane disruption.

The peptides designed to have primarily a $3_{10}$-helix secondary structure comprise 6 to 15 residues, preferably 6 to 10 residues. The peptides contain 50 to 100% residues that are α,α-dialkylated amino acids. The peptides also contain 25 to 50% polar amino acid residues such that the peptide has an overall positive charge under physiological conditions, and 50 to 75% nonpolar α,α-dialkylated amino acid residues. The nonpolar residues and the polar residues are distributed within the peptide such that when the peptide forms a $3_{10}$-helix under physiological conditions, the nonpolar residues align on one face of the $3_{10}$-helix, with the polar residues on the opposite face of the $3_{10}$-helix, making the peptide amphipathic. Without wishing to be bound by this theory, it is believed that a $3_{10}$-helix of only 6 residues long can cause membrane disruption. A $3_{10}$-helix is a tighter, longer molecule than an α-helix with the same number of residues.

A series of amphipathic helical peptides comprising 50–80% α,α-dialkylated amino acids was synthesized and assayed for activity against bacterial pathogens. These peptides incorporated α,α-dialkylated amino acids that were only nonpolar residues, or were a combination of nonpolar and polar residues. The secondary structure of these peptides was either an α- or $3_{10}$-helix in membrane mimetic media. Synthesis was conducted on solid phase resin as C-terminus amides using standard α-N-fluorenylmethoxycarbonyl (Fmoc) protection and acid fluoride coupling methods. The amino acids α-amino-isobutyric acid. (Aib), 1-aminocyclohexanecarboxylic acid (Ch), and 4-aminopiperidine-4-carboxylic acid (Api), were incorporated along with lysine, the latter being the only chiral amino acid used. Api, introduced as the γ-tert-butoxycarbonyl derivative, is a novel, lysine-like, α,α-dialkylated amino acid with a positively charged side chain at physiological pH. To be used in peptide synthesis, a Fmoc-protected derivative was first prepared. Additionally, new cationic α,α-dialkylated amino acids were synthesized for incorporation into peptides.

The synthetic peptides showed antibacterial activity against *Escherichia coli* and *Staphylococcus aureus*, but no direct in vitro activity against *Brucella abortus*. Surprisingly, in vivo several of these peptides caused significant reductions of *B. abortus* in chronically infected BALB/c mice relative to controls. Without wishing to be bound by this theory, it appears that these peptides reduced the bacterial load in vivo by destroying infected macrophages, and exposing the sequestered bacteria to the normal immune response of the mice. In addition, the peptides selectively destroyed *B. abortus*-infected murine macrophages in vitro.

Synthesis of Novel Polar α,α-Dialkylated Amino Acids

Four novel polar α,α-dialkylated amino acids were synthesized from the starting compound of 1,4-cyclohexane dione mono-ethylene ketal, purchased from Aldrich Chemical Co. (Compound 1 in FIG. 1) and the amine of ethyl (R=a), n-butyl (R=b), phenylmethyl (R=c), or 2-naphthylmethyl (R=d).

Step 1: Synthesis of Compound 2(a–d). Reductive amination conditions were according to Abdel-Magid et al., Tetrahedron Letters, vol. 31, pp. 5595–5598 (1990). Under argon, Compound 1 (32 mmol) was dissolved in 50 mL of 1,2-dichloroethane followed by the addition of acetic acid (32 mmol). The desired amine (a–d) (35.2 mmol) was added, and the reaction was stirred for 30 minutes at room temperature. At this time $NaBH(OAc)_3$ (51.3 mmol) was added and stirred overnight. The reaction mixture was diluted with 100 mL of 1,2-dichloroethane and poured onto 150 mL of a 10% $Na_2CO_3$ solution and extracted. The organic layer was washed twice more with 150 mL 10% $Na_2CO_3$ solution, dried over $MgSO_4$, and concentrated under reduced pressure.

Step 2: Synthesis of Compound 3(a–d). In a flask fitted with a reflux condenser and a mercury bubbler, Compound 2 (31 mmol) was dissolved in 55 mL of tetrahydrofuran (THF), and 19 mL of a 20% trifluoroacetic acid (TFA) solution was added. The resulting solution was heated to reflux. After 24 hr the solvents were removed and the oil was taken up in methylene chloride. This solution was then washed three times with 150 mL of a 10% $Na_2CO_3$ solution. The organic layer was dried over $MgSO_4$, and the excess solvent removed under reduced pressure.

Step 3: Synthesis of Compound 4(a–d). In a flask equipped with a mercury bubbler, $Et_3N$ (30 mmol), $(Boc)_2$-O (36 mmol), and 4-N,N-dimethylaminopyridine (DMAP) (3.0 mmol) were sequentially added at 5 minute intervals to a solution of Compound 3 in 100 mL of methylene chloride. The mixture was stirred at room temperature for 24 hours. The resulting solution was washed with 1 N HCl (2×75 mL), 10% $Na_2CO_3$ (1×75 mL) and brine (1×75 mL), dried over $MgSO_4$, and concentrated under reduced pressure.

Step 4: Synthesis of Compound 5(a–d). A 25 mL solution of $(NH_4)_2CO_3$ (70 mmol) and KCN (70 mmol) was added to a solution of Compound 4 (28 mmol) in 25 mL of methanol and refluxed for two days. The flask was allowed to cool and the resulting precipitate was filtered and washed with water. The brown solid was taken up in methylene chloride and precipitated by the slow addition of hexane. The solid was filtered and dried under vacuum.

Step 5: Synthesis of Compound 6(a–d). $(Boc)_2$-O (24 mmol) and Compound 5 (6.1 mmol) were placed in a flask fitted with a mercury bubbler and dissolved in 100 mL of THF. After five minutes, DMAP (0.61 mmol) was added and the mixture was stirred overnight. The THF was removed, and the solid was taken up in methylene chloride. This solution was washed with 1 N HCl (2×75 mL), 10% $Na_2CO_3$ (1×75 mL) and brine (1×75 mL), dried over $MgSO_4$, and concentrated under reduced pressure.

Step 6: Synthesis of Compound 7(a–d). In a round bottom flask, 6 (1.85 mmol) was dissolved in 165 mL of THF, followed by addition of 15 mL of 1 N LiOH. The reaction mixture was stirred vigorously overnight, and was concentrated under reduced pressure to remove most of the THF. The resulting solution was washed with ether, and the pH adjusted to 7. The solid that precipitated from the pH 7 aqueous solution was filtered off and dried under vacuum.

The new compounds are the following: (1) from R=a, 1-amino-4-(N-tert-butyloxycarbonyl-N-ethylamino)cyclohexanecarboxylic acid; (2) from R=b, 1-amino-4-(N-tert-butyloxycarbonyl-N-butylamino)cyclohexanecarboxylic acid; (3) from R=c, 1-amino-4-(N-tert-butyloxycarbonyl-N-phenylmethylamino)cyclohexanecarboxylic acid; and (4)

from R=d, 1-amino-4-(N-tert-butyloxycarbonyl-N-naphthylmethylamino)cyclohexane carboxylic acid. To incorporate these new cationic α,α-dialkylated amino acids into peptides the Fmoc-protected derivative of each was prepared as discussed below.

Step 7: Synthesis of Compound 8(a–d). The method of Bolin et al., International Journal of Peptide and Protein Research, 1989, pp. 353–359 (1989), was adapted to prepare the $N^\alpha$-Fmoc derivatives of the amino acids. The free amino acid Compound 7 (0.88 mmol) was suspended in 75 mL of dry methylene chloride, and DIEA (2.64 mmol) was added and stirred for 5 minutes. Trimethylsilyl chloride (2.2 mmol) was added, and the solution was refluxed for 3 hours. The flask was cooled in an ice bath for 20 minutes and Fmoc-Cl (1.0 mmol) was added. The mixture was stirred overnight and allowed to warm slowly to room temperature. The resulting product was washed with 1 N HCl, and the solvent removed under reduced pressure. The solid was purified by column chromatography over silica gel using a chloroform/methanol mixture (ratios ranging from 9:1 to 95.5:0.5).

Synthesis of Fmoc-Protected Polar α,α-Dialkylated Amino Acids

α,α-Dialkylated amino acids (Compound 1 below, $R^1$, $R^2$=alkyl, or substituted polar alkyl;≠H) have been used as replacements for proteinogenic amino acids in peptides because of their strong secondary structure promoting effects and the increased proteolytic stability of the resulting peptides. α,α-Dialkylated amino acids have been previously incorporated into and studied in peptides; however, all prior α,α-dialkylated amino acids have been hydrophobic. Hydrophilic α,α-dialkylated amino acids have not been previously incorporated into peptides. To incorporated these polar amino acids into proteins, the hydrophilic, charged side group must be protected. The following procedure was developed to make a protected derivative that could be used in peptide synthesis.

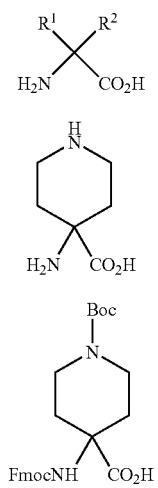

The achiral "cationic" α,α-dialkylated amino acid 4-aminopiperidine-4-carboxylic acid (Compound 2 above, Api) has a γ-nitrogen that will be protonated under the usual conditions of bioactivity assays (pH<9.0) A $N^\alpha$-Fmoc, $N^\gamma$-Boc protected 4-amino-piperidine-4-carboxylic acid [Fmoc-Pip(Boc)-OH, (Compound 3 above)] was synthesized and then incorporated into peptides using Fmoc solid-phase synthesis methods.

Figure 2:
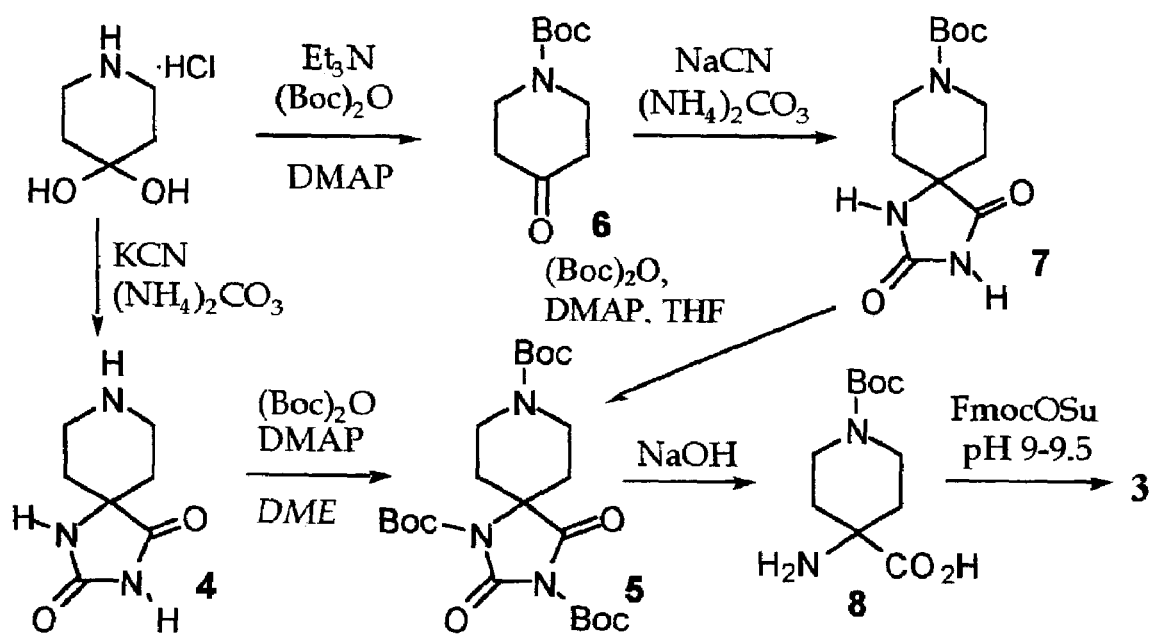
FIG. 2 illustrates a synthetic pathway for the $N^\alpha$-Fmoc, $N^\gamma$-Boc protected derivative of a cationic α,α-dialkylated amino acid, 4-amino-piperidine-4 carboxylic acid.

In general, the synthesis of Compound 3, as illustrated in FIG. 2, starts with the formation of hydantoin, Compound 4, from 4-piperidone by a Bucherer-Bergs procedure. To obtain a protected derivative suitable for solid-phase Fmoc strategy, all the nitrogen functionalities of hydantoin 4 were protected with Boc groups, and then the α-amino and α-acid moieties were unmasked by mild treatment with hydroxide, which left the $N^\gamma$-position still protected with a Boc group. This strategy avoided separate steps such as copper complex formation, which is often required to differentially protect α-amine and side-chain groups in tri-functional amino acids like lysine. Early attempts to form the tris-Boc hydantoin (Compound 5) in THF were unsuccessful because of the low solubility of hydantoin 4. Other solvents such as N,N-dimethylformamide (DMF) or dimethyl sulfoxide (DMSO) required heating to initiate the reaction, leading to low yields of colored products. As an interim solution, piperidone was protected with a Boc group (Compound 6) and converted to the $N^\gamma$-Boc-hydantoin 7, which had greatly improved solubility and was easily converted to the tris-Boc hydantoin 5 quantitatively in THF (40% yield from 4-piperidone). Ultimately, the best condition found that allowed direct conversion of hydantoin 4 to tris-Boc hydantoin 5 used 1,2-dimethoxyethane (DME) as solvent at room temperature, producing 5 in excellent yield (72% from 4-piperidone).

To reveal the amino acid functionality, fully protected 5 was treated with hydroxide to produce $N^\gamma$-Boc-4-amino-piperidine-4-carboxylic acid (Compound 8) with concomitant formation of di-tert-butyl imidodicarbonate ($Boc_2NH$). Isolated yields of $N^\gamma$-Boc-protected 8 were often low and contaminated with salts, so a one-pot procedure for conversion of tri-Boc hydantoin 5 to 3 was developed. Thus, the above cleavage reaction containing 8 was extracted with ether to remove $Boc_2NH$ and then Fmoc-OSu was added along with NaOH to keep the pH~9, giving Compound 3 in 63% overall yield from 4-piperidone.

Source and Preparation of Chemicals. THF was dried over KOH and distilled over potassium prior to use. All other solvents were used as purchased, and were of the highest grade commercially available. The 4-piperidinone monohydrate hydrochloride was purchased from Lancaster Chemical Company. Sodium cyanide was purchased from Aldrich Chemical Company (ReagentPlus™, 99.99%) or Mallinckrodt Chemical (99.9%). Powdered ammonium carbonate (preferred for convenience) was purchased from Fisher Chemicals; ammonium carbonate chunks (less desirable) were purchased from Aldrich or Mallinckrodt. $Boc_2O$ and N-(9-fluorenylmethyloxycarbonylosy)succinimide (Fmoc-OSu) were purchased from Advanced ChemTech.

Step 1: Synthesis of Piperidine-4-spiro-5'-hydantoin (4). A solution of NaCN (17.0 g, 347 mmol) in $H_2O$ (50 mL) was added dropwise over 5 min to a solution of 4-piperidone monohydrate hydrochloride (25.0 g, 163 mmol) and $(NH_4)_2CO_3$ (chunks, 34.5 g, 359 mmol) in $H_2O$ (90 mL) and $CH_3OH$ (110 mL). An off-white precipitate began to form soon after addition was complete. The reaction flask was sealed and the suspension stirred at room temperature for an additional 2 days. The resultant light yellow precipitate was isolated by filtration and washed with small portions of $H_2O$ until almost pure white. Yield: 24.0 g (87%); mp>300° C. A second crop was obtained from the filtrate by evaporation of most of the solvent and dilution with $H_2O$ (100 mL), filtration, and repeated washings with $H_2O$. Yield: 1.5 g, mp>300° C. Overall yield: 25.5 g (93%). Almost identical yield and purity of 4 were obtained when the same procedure was used, except that after NaCN addition, the flask was sealed and heated to 50° C. for 48 hrs. $^1H$ NMR (250 MHZ, CD$_3$SOCD$_3$) d 10.75 (bs, 1H), 8.46 (s, 1H), 2.83 (app dt, J≈13, 4 Hz, 2H), 2.67 (app dt, J≈12, 2 Hz, 2H), 1.67 (app dt, J≈12, 4 Hz, 2H), 1.39–1.34 (m, 2H). $^{13}$C NMR (50 MHZ, CD$_3$SOCD$_3$) d 177.99, 156.27, 61.01, 41.13, 33.81. MALDI-MS (DHB) m/z 170 (M+H)$^+$. Analysis calculated for C$_7$H$_{11}$N$_3$O$_2$ (169.18): C, 49.70; H, 6.55; N, 24.84; found: C, 49.48; H, 6.52; N, 25.00.

Step 2: Synthesis of 1-Boc-piperidine-4-spiro-5'-(1',3'-bis-Boc)-hydantoin (5). In a flask fitted with an oil bubbler, piperidine hydantoin (4) (15.3 g, 90.5 mmol) was suspended in DME (450 mL). Boc$_2$O (102 g, 468 mmol), 4-N,N-dimethylaminopyridine (DMAP) (0.22 g, 1.64 mmol), and Et$_3$N (12.8 mL; 91.9 mmol) were added in succession. CO$_2$ evolution was vigorous at the initial addition of DMAP and continued at a steady pace (1 bubble/20–40 sec). After 3 hrs, an additional portion of DMAP (0.2 g, 1.64 mmol) was added, and the reaction mixture stirred for another 18 hrs. The mixture was concentrated under reduced pressure to yield a solid which was taken up in CH$_2$Cl$_2$ (500 mL), washed with 1 N HCl (2×75 mL), saturated aqueous Na$_2$CO$_3$ (1×100 mL), brine (1×100 mL), dried over anhydrous MgSO$_4$, filtered and concentrated to yield a light creamy white solid (42.4 g, quantitative), mp 186–190° C. $^1$H NMR (250 MHZ, CDCl$_3$) d 4.18–4.03 (dd, 1H), 3.38 (bt, 1H), 2.67 (dt, J-5.3 Hz, 13.1 Hz, 1H), 1.77–1.71 (d, 1H), 1.57 (s, 9H), 1.52 (s, 9H), 1.46 (s, 9H); $^{13}$C NMR (50 MHZ, CDCl$_3$) d 169.73, 154.44, 148.01, 147.24, 145.11, 86.85, 85.09, 79.87, 39.43, 29.62, 28.37, 27.96, 27.82, 27.65; Analysis calculated for C$_{22}$H$_{35}$N$_3$O$_8$ (469.54): C, 56.28; H, 7.51; N, 8.95; found: C, 56.10; H, 7.72; N, 8.99.

Step 3: Synthesis of 1-Boc-piperidine-4-Fmoc-amino-4-carboxylic acid (3). 1 N NaOH (287 mL, 287 mmol) was added all at once to a suspension of tri-Boc-hydantoin 5 (15.0 g, 32.0, mmol) in DME (200 mL), resulting in a homogeneous solution. After 26 hrs, the resulting light yellow solution was extracted with Et$_2$O (3×75 mL) to remove Boc$_2$NH. The aqueous layer containing 4-amino-1-Boc-piperidine-4-carboxylic acid (8) from above was cooled in an ice bath and the pH adjusted to 9.5 with 12 N HCl. This prechilled solution was added dropwise to a chilled mixture (ice-bath) of Fmoc-OSu (16.0 g, 47.4 mmol) in DME (40 mL). A precipitate formed immediately, and the reaction mixture was allowed to warm to room temperature, keeping the pH at 9.0–9.5 by addition of 1 N NaOH; total reaction time: 18 h. The DME was removed in vacuo (<40° C.) and the resultant aqueous layer was extracted with Et$_2$O (2×50 mL) to remove unreacted Fmoc-OSu. The aqueous fraction was chilled with an ice bath and adjusted to pH 4 with 12 N HCl and extracted with EtOAc (4×250 mL). The combined EtOAc layers were washed with 1 N HCl (100 mL), brine (100 mL), dried (Na$_2$SO$_4$), and the solvent removed in vacuo to yield a light yellow powder (10.8 g, 87%); mp 80–82° C. $^1$H NMR (200 MHz, CD$_3$SOCD$_3$) d 8.30 (s, 1H), 7.85–7.96 (d, 2H), 7.70–7.80 (d, 2H), 7.22–7.54 (m, 4H), 4.19–4.32 (m, 3H), 3.55–3.76 (m, 2H), 2.90–3.09 (m, 2H), 1.91–2.15 (m, 2H), 1.65–1.89 (m, 2H), d 1.39 (s, 9H); $^{13}$C NMR (50 MHZ, CD$_3$SOCD$_3$) d 175.36, 155.26, 153.83, 143.76, 140.67, 127.54, 126.98, 125.21, 119.99, 79.11, 78.56, 65.26, 56.73, 46.72, 31.26, 28.01; FAB-MS (NBA) 467 (M+H)$^+$, 367 [(M+H)-Boc]$^+$; Analysis calculated for C$_{26}$H$_{30}$N$_2$O$_6$.H$_2$O (484.55): C, 64.45; H, 6.66; N, 5.78; found: C, 64.48; H, 6.87; N, 5.74.

Step 4: Synthesis of 1-Boc-4-aminopiperidine-4-carboxylic acid (8). In a 2L Erlenmeyer flask equipped with a stirring bar, 1-Boc-4-piperidinespiro-5'-(di-t-Boc)-hydantoin (5) (4.23 g, 9.0 mmol) was suspended in THF (800 mL). To this suspension was added 1N LiOH (72 mL, 72 mmol) with vigorous stirring. The resulting white suspension was stirred for 24 hrs. The final reaction mixture was concentrated with reduced pressure, extracted with Et$_2$O (2×125 mL), and the pH adjusted to 7 with a solution of 20% citric acid. The resulting solid was filtered and dried in vacuo to yield 1-Boc-4-aminopiperidine-4-carboxylic acid 8 (1.54 g, 70%). $^1$H NMR (250 MHZ, C$_5$D$_5$N) d 4.45 (br, 1H), 4.23 (br, 1H), 3.71 (br, 2H), 2.87 (dt, 2H), 2.35 (br, 1H), 1.86 (br d, 2H), 1.55, 1.54 (2s, 9H).

Step 5: Synthesis of 1-Boc-piperidine-4-Fmoc-amino-4-carboxylic acid (3). From the above cleavage reaction containing Compound 8, the mixture was extracted with ether to remove Boc$_2$NH and then Fmoc-OSu was added along with NaOH to keep the pH~9 giving Compound 3 in 63% overall yield from 4-piperidone. $^{13}$C NMR (50 MHZ, CD$_3$SOCD$_3$) d 175.36, 155.26, 153.83, 143.76, 140.67, 127.54, 126.98, 125.21, 119.99, 79.11, 78.56, 65.26, 56.73, 46.72, 31.26, 28.01; FAB-MS (m-nitrobenzylalcohol) 467 (M+H)$^+$, 367 [(M+H)-Boc]$^+$; Analysis calculated for C$_{26}$H$_{30}$N$_2$O$_6$.H$_2$O (484.55): C, 64.45; H, 6.66; N, 5.78; found: C, 64.48; H, 6.87; N, 5.74.

An alternate route to Compound 5 was first tried but was more time consuming because two intermediate compounds (Compounds 6 and 7) were made instead of only one (Compound 4) in the preferred method described above. The alternate route is described below.

Step 1: Synthesis of 1-Boc-4-piperidone (6). To a suspension of 4-piperidinone monohydrate hydrochloride (20.0 g, 130.2 mmol) in dry THF (300 mL) was added triethylamine (19.25 g, 190.3 mmol). After 5 minutes of vigorous stirring, Boc$_2$O (34.6 g, 158 mmol) was added along with a catalytic amount of DMAP (0.33 g, 2.7 mmol). After stirring overnight at room temperature, the reaction mixture was concentrated under reduced pressure, the residue taken up in CH$_2$Cl$_2$ (100 mL), washed with 2N HCl (2×70 mL), saturated aqueous Na$_2$CO$_3$ (1×70 mL), brine (1×50 mL), dried (MgSO$_4$) and then concentrated to yield a light tan solid (19.7 g, 75%); mp 64–65° C. (compared to previously reported mp's of 70–72° C. or 74–75° C.); $^1$H NMR (250 MHZ, CDCl$_3$) d 3.71 (t, J=6.1 Hz, 2H), 2.44 (t, J=6.2 Hz, 2H), 1.49 (s, 9H); $^{13}$C NMR (62.5 MHZ, CDCl$_3$) d 207.71, 153.54, 80.44, 43.08, 41.20, 28.45; FAB-MS (glycerol) m/z 200 ((M+H)$^+$), 144 ((M+H)$^+$—C$_4$H$_8$)); Analysis calculated for C$_{10}$H$_{17}$NO$_3$ (199.25): C, 60.28; H, 8.60; N, 7.03; found: C, 59.98; H, 8.46; N, 7.04.

Step 2: Synthesis of 1-Boc-piperidine-4-spiro-5'-hydantoin (7). In a 1L round bottom flask equipped with a stirring bar, 1-Boc-4-piperidone (15.0 g, 75.4 mmol) and (NH$_4$)$_2$CO$_3$ (22.8 g, 234 mmol) were suspended in a mixture of CH$_3$OH (110 mL) and H$_2$O (90 mL). To this suspension was slowly added dropwise over 15 min a solution of NaCN (3.92 g, 80.0 mmol) in H$_2$O (25 mL). The reaction flask was then sealed and treated as above. Yield: 14.9 g, 74%; m.p 233–234° C. (dec.). $^1$H NMR (250 MHZ, CD$_3$SOCD$_3$) d 10.73 (bs, 1H), 8.49 (s, 1H), 3.83–3.71 (dd, 2H), 3.11 (bs, 1H), 1.67 (dt, J=4.3 Hz, 12.2 Hz, 2H), 151 (br dt, J=13.4 Hz, 2H), 1.39 (s, 9H); $^{13}$C NMR (62.5 MHZ, d$_6$-DMSO) d 177.72, 156.45, 153.82, 78.84, 60.00, 32.64, 27.99; FAB-MS (glycerol) m/z 270 ((M+H)$^+$), 214 ((M+H)$^+$—C$_4$H$_8$). Analysis calculated for C$_{12}$H$_{19}$N$_3$O$_4$ (269.30): C, 53.52; H, 7.11; N, 15.60; found: C, 53.36; H, 6.96; N, 15.61.

Peptide Synthesis

The preferred peptides comprise 50–80% α,α-dialkylated amino acids. Combinations of lysine with Aib or 1-amino-1-cyclohexanecarboxylic acid (Ch), and combinations of lysine with Aib and the novel amino acid 4-aminopiperidine- 4-carboxylic acid ("Api" or "Pip") (See structures below) were incorporated into embodiments of the peptides. The peptides synthesized to date are listed in Table 1.

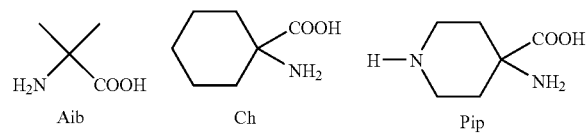

mated Solid Phase Synthesis of Naturally Occurring Peptaibols Using Fmoc Amino Acid Fluorides," Journal of Organic Chemistry, vol. 60, pp. 405–410 (1995).

The only synthetic difficulty encountered came in coupling the second residue in the Ch-11 (SEQ ID No. 5) and Ch-14 peptides (SEQ ID No. 4). This problem was overcome by manually performing the first three coupling steps. The resin was suspended in 1,2-dichloroethane and refluxed until small samples of resin showed that the coupling was greater than 90% complete according to Fmoc deprotection analysis. The synthesized peptides were amphipathic, and

TABLE 1

List of Synthesized Peptides

| | | |
|---|---|---|
| Al-14 | H-LysAlaAlaLysLysAlaAlaLysAlaAlaLysLysAlaAla-NH$_2$ | (SEQ ID No. 1) |
| Ai-14 | H-LysAibAibLysLysAibAibLysAibAibLysLysAibAib-NH$_2$ | (SEQ ID No. 2) |
| Ai-11 | H-LysLysAibAibLysAibAibLysLysAibAib-NH$_2$ | (SEQ ID No. 3) |
| Ai-11-ac | Ac-LysLysAibAibLysAibAibLysLysAibAib-NH$_2$ | (SEQ ID No. 3) |
| Ch-14 | H-LysChChLysLysChChLysChChLysLysChCh-NH$_2$ | (SEQ ID No. 4) |
| Ch-11 | H-LysLysChChLysChChLysLysChCh-NH$_2$ | (SEQ ID No. 5) |
| Ch-13 | H-LysChChLysLysChChLysChChLysLysCh-NH$_2$ | (SEQ ID No. 6) |
| Ch-10 | H-LysLysChChLysChChLysLysCh-NH$_2$ | (SEQ ID No. 7) |
| Pi-10 | H-AibAibApiLysAibAibApiLysAibAib-NH$_2$ | (SEQ ID No. 8) |
| Pi-10-ac | Ac-AibAibApiLysAibAibApiLysAibAib-NH$_2$ | (SEQ ID No. 8) |
| Ipi-10 | H-ApiAibAibLysAibAibLysAibAibApi-NH$_2$ | (SEQ ID No. 9) |
| Ipi-10-ac | Ac-ApiAibAibLysAibAibLysAibAibApi-NH$_2$ | (SEQ ID No. 9) |

The first peptide, A1–14 (SEQ ID No. 1), was synthesized using standard Fmoc (fluorenyl methyloxycarbonyl) solid-phase synthesis methods using a MilliGen 9050 Pep Synthesizer. This peptide was used for activity comparisons against the peptides containing α,α-dialkylated amino acids. The peptide was cleaved and deprotected with a trifluoroacetic acid based reagent (88% trifluoroacetic acid (TFA), 5% water, 5% phenol, 2% triisopropylsilane) for 2–4 h, dried, taken up in cold 20% acetic acid, extracted with diethyl ether, and lyophilized. The peptide was then purified by reverse phase preparative HPLC on a Waters 15-μ Deltapak C$_4$ column, 200×25 mm, using a mobile phase of acetonitrile (0.05% v/v TFA) and water (0.05% v/v TFA), running a gradient of 10–50% of the organic phase over one hour. Purity was checked on an analytical Vydac 5-μ C$_{18}$ column running a similar mobile phase gradient and monitoring at 220 nm. The molecular weight of purified peptide was verified by plasma desorption mass spectrometry on a BioIon 20. The peptide was stored as lyophilized powder at −20° C.

The remaining peptides were synthesized via Fmoc chemistry using preformed acid fluorides on a PAL resin to yield C-terminus amides. The current state of peptide synthesis methods allows relatively simple solid-phase synthesis of Aib or Aib-like rich peptides. See, e.g., Wenschuh et al., "Fmoc Amino Acid Fluorides: Convenient Reagents for the Solid-Phase Assembly of Peptides Incorporating Sterically Hindered Residues," Journal of Organic Chemistry, vol. 59, pp. 3275–3280 (1994); Wenschuh et al., "Stepwise Autoshowed good in vitro antibacterial activity. To maximize the number of α,α-dialkylated amino acids and retain a high level of positive charge on the polar face of the peptides, the lysine-like α,α-dialkylated amino acid Api was introduced.

With Fmoc-Api(Boc)-OH (Compound 3 in FIG. 2, synthesis described above) in hand, the two sequence permutation isomers H-Aib-Aib-Api-Lys-Aib-Aib-Api-Lys-Aib-Aib-NH$_2$ (Pi-10, SEQ ID No. 8) and H-Api-Aib-Aib-Lys-Aib-Aib-Lys-Aib-Aib-Api-NH$_2$ (Ipi-10, SEQ ID No. 9) were prepared by automated solid-phase Fmoc chemistry on a PAL-PEG-PS support. Pi-10 and Ipi-10 were prepared in automated fashion using preformed acid fluorides (synthesis described below) This method worked well for Pi-10 producing material that was 78% pure as measured by reversed-phase HPLC; however, the synthesis of Ipi-10 failed to give full-length product. This initial failure was traced to problems with the initial three C-terminal α,α-dialkylated amino acid couplings to the resin when using standard acid fluoride cycles. This difficulty was perhaps due to steric crowding around the PAL-linker/resin attachment point, exacerbating the steric hindrance inherent in the protected α,α-dialkylated amino acids. This problem was alleviated by coupling the first three amino acid fluorides in refluxing CH$_2$Cl$_2$ or 1,2-dichloroethane for extended periods. Thus, the first three acid fluorides (1.6 mmol, 8 equiv) with DIEA (0.56 mL, 3.2 mmol, 2 equiv) were coupled off the machine onto the deblocked resin (1.34 g, 0.2 mmol) in refluxing CH$_2$Cl$_2$ (10 mL, 0.16 M of amino acid, 0.32 M DIEA) overnight. After washing with CH$_2$Cl$_2$ (4×30 mL), deblocking was performed with DBU-piperidine-DMF (2:20:80; 1×1 min, 1×10 min) and the resin washed with $CH_2Cl_2$ (5×30 sec) and coupled to the next acid fluoride using the same method. After the third coupling, the resin was placed on the instrument and couplings, cleavage and purification thereafter were accomplished by the standard methods. The rest of the synthesis went smoothly with standard automated acid fluoride couplings, giving a crude Ipi-10 that was 36% pure by HPLC. Both peptides were readily purified to homogeneity by preparative HPLC.

Pi-10 and Ipi-10 were readily soluble in water without any organic modifier present. Circular dichroism (CD) studies in the presence of SDS micelles showed very high helicity. Pi-10 showed a CD indicative of 43% α-helix, consistent with its amphipathic design. Ipi-10, designed to be an amphipathic $3_{10}$-helix, also showed a highly helical structure in the presence of SDS micelles, but in contrast had a distinctively different CD spectrum with a strong negative ellipticity at 206 nm (−5000 θ) and a low 222/206 intensity ratio (0.32), which is strongly indicative of a $3_{10}$-helix.

To prepare the acid fluoride of the Fmoc protected derivative, Carpino's method was used (Wenschuh et al., 1994). A solution of Fmoc-piperidine amino acid 3 (3.0 g, 6.4 mmol) and pyridine (0.55 mL, 6.4 mmol) in dry $CH_2Cl_2$ (100 mL) was treated by cooling (ice bath) under argon with cyanuric fluoride (1.10 mL, 12.8 mmol). After 4 hrs, the solution was poured onto ice water (250 mL) and shaken. The entire solution was filtered and the organic layer was separated, dried ($MgSO_4$) and evaporated in vacuo to yield a tan solid (2.43 g, 81%); $^1H$ NMR (200 MHz, $CD_3SOCD_3$) d 1.40 (s, 9H), 1.75–2.10 (m, 4H), 2.90–3.20 (m, 2H), 3.52–3.71 (m, 2H), 4.18–4.28 (t, 1H), 4.40–4.51 (d, 2H), 7.30–7.48 (m, 5H), 7.70–7.78 (d, 2H), 7.80–7.95(d, 2H), 8.30 (s, 1H).

Without limiting the scope of the invention, examples of other nonpolar α,α-dialkylated amino acids that may prove especially effective include di-ethyl glycine, di-n-propyl glycine, isovaline (α-ethylalanine), $C^α$-methylvaline, $C^α$-methylleucine, 1-amino-cyclopropanecarboxylic acid, 1-amino-cyclobutanecarboxylic acid, 1-amino-cyclopentanecarboxylic acid, 1-amino-cyclohexanecarboxylic acid, 1-amino-cycloheptanecarboxylic acid, and 1-amino-cyclooctanecarboxylic acid.

Without limiting the scope of the invention, examples of other polar residues that may prove especially effective include arginine, histidine, 1-amino-4-(N-ethylamino)cyclohexanecarboxylic acid, 1-amino-4-(N-butylamino)cyclohexanecarboxylic acid, 1-amino-4-(N-phenylmethylamino)cyclohexanecarboxylic acid, and 1-amino-4-(N-naphthylmethylamino)cyclohexanecarboxylic acid, glycine, serine, threonine, tyrosine, cysteine, glutamine, asparagine, aspartic acid, glutamic acid, 3-aminoazetidine-3-carboxylic acid, 1-amino-1,3-cyclopentanedicarboxylic acid, 3-amino-bicyclo[3,3,0]octane-1,3-dicarboxylic acid, and hydroxymethylserine.

Assay Procedures

In Vitro Antibacterial Activity

To test for in vitro antibacterial activity, minimum inhibitory concentrations (MIC) assays for eight of the peptides were measured against *Escherichia coli*, ATCC 25922, a Gram-negative bacterium, and *Staphylococcus aureus*, ATCC 25723, a Gram-positive bacterium. Peptide 1:2 serial dilutions were prepared from 512 μg/mL stock solutions to give a range of 256–2 μg/mL in the culture media. Bacterial cultures were grown to mid-log phase in nutrient broth and were standardized against a 0.5 McFarland turbidity tube before dilution. To each sterile well containing $5×10^4$ cells in 50 μL, an equal volume of peptide solution was added. The MIC was the lowest concentration that inhibited cell growth as evidenced by absence of turbidity after 4 h. The median assay values are reported for 3–7 separate tests. Assay results varied by no more than one dilution from the median value. Table 2 presents the results of this study.

TABLE 2

Peptide minimum inhibitory concentration[a] and percent helicity.

| Peptide | E. coli | S. aureus | % Helicity[b] |
|---|---|---|---|
| A1-14 SEQ ID No. 1 | >178 | >178 | ND[c] |
| Ai-14 SEQ ID No. 2 | 5.5 | 11 | 42 |
| Ai-11 SEQ ID No. 3 | 55 | >220 | 35 |
| Ai-11-ac SEQ ID No. 3 | 6.6 | 212 | ND[d] |
| Ch-13 SEQ ID No. 6 | 6.5 | 2.2 | 61 |
| Ch-11 SEQ ID No. 5 | 5.2 | 2.6 | ND[d] |
| Ch-10 SEQ ID No. 7 | 5.7 | 2.8 | 43 |
| Pi-10 SEQ ID No. 8 | 7.7 | 123 | 43 |
| Ipi-10 SEQ ID No. 9 | 4.0 | >256 | |
| Ipi-10-Ac SEQ ID No. 9 | 8.0 | | |

[a]These MIC in μM are corrected for the actual peptide concentration using quantitative amino acid analysis according to Javadpour et al., "De Novo Antimicrobial Peptides with Low Mammalian Cell Toxicity," Journal of Medicinal Chemistry, vol. 39, pp. 3107–3113 (1996).
[b]The % α helix = −100 ([θ]$_{222}$ + 3000)/33000; [θ]$_{222}$ = [θ]$_{obs}$(MRW/101c) taken in 25 mM SDS micelles with 100–200 μM peptide according to McLean et at., "Minimal Peptide Length for Interaction of Amphipathic α-Helical Peptides with Phosphatidylcholine Liposomes, "Biochemistry, vol. 30, pp. 31–37 (1991).
[c]This peptide precipitates when the 25 mM SDS is added, precluding CD spectroscopic measurement.
[d]Insufficient quantities of these peptides were made for CD spectroscopic measurements.

The replacement of Ala residues in A1–14 (SEQ ID No. 1) with Aib residues in Ai-14 (SEQ ID No. 2) had a substantial effect on the biological activity. Ai-14 (SEQ ID No. 2) was at least 8–16 times more active than A1–14 (SEQ ID No. 1). A1–14 (SEQ ID No. 1) precipitated out of 25 mM SDS micelles so a comparison of secondary structure was precluded. Shortening Ai-14 (SEQ ID No. 2) to make Ai-11 (SEQ ID No. 3) resulted in diminished, but measurable activity against *E. coli*, but no activity against *S. aureus*.

While Aib helps to promote helical conformations, it is not a very hydrophobic residue. The Ch residue was introduced to determine whether greater hydrophobic character would increase the activity of peptides with otherwise similar designs. Ch-13 (SEQ ID No. 6) had essentially the same activity as its closest Aib peptide counterpart, Ai-14 (SEQ ID No. 2). However, Ch-10 (SEQ ID No. 7) with only 10 residues had similar activity to Ch-13 (SEQ ID No. 6), but much higher activity than its closest Aib peptide counterpart, Ai-11 (SEQ ID No. 3). Pi-10 (SEQ ID No. 8) with only 10 residues and only two natural amino acids also showed good antibacterial activity against *E. coli* and moderate activity against *S. aureus*.

*Brucella abortus* is one of the few bacteria resistant to the direct antimicrobial effect of these peptides in vitro. Stock cultures of virulent *B. abortus* strain 2308 were passaged in BALB/c mice and isolated in pure culture from spleens.

Stock cultures were prepared from 48-hour growth on Schaedler blood agar plates and stored at −80° C. For infection assays, contents of freshly thawed vials were diluted with sterile phosphate buffered saline (PBS) to establish a concentration of $5\times10^5$ colony forming units (CFU) per ml. Exact numbers were established by viability counts. Stocks for use in the macrophage assays (below) were derived from the stocks above from a single solid agar passage of the strain.

B. abortus, strain 2308, was adjusted to a concentration of $1\times10^8$ CFU per mL of PBS. Various peptides were added to obtain a final concentration 10 μM peptide per $1\times10^8$ CFU of B. abortus. Viable counts were performed at 5, 30, and 60 min post-peptide treatment. There were no observed differences with any of the peptides tested in vitro against *B. abortus* compared with PBS controls.

In Vivo Activity Against *Brucella*

In vivo peptide activity was tested using BALB/c mice infected with a virulent strain of *B. abortus*. Female BALB/c mice were purchased at 9 weeks of age from the Department of Laboratory Animal Medicine at the Louisiana State University School of Veterinary Medicine's breeding colony. The animals were held for 1 week before use. Mice were infected intravenously with approximately $5\times10^4$ CFU of *B. abortus* strain 2308 in 100 μL of PBS via the lateral tail vein. Both humoral and cell-mediated immune responses developed 3–4 weeks after the infection of the mice. Both of these responses are necessary to control the infection, but seldom do they eliminate the infection because the organism "hides" within macrophages. After 4 weeks, the mice were treated intravenously with peptide (treated animals) or with saline (control animals). The mice were observed after injection of the peptide for signs of stress (tremors, respiratory difficulty, or paralysis) or death. After 24 hours the mice were killed by $CO_2$ asphyxiation, their spleens and livers were aseptically removed, and small sections were fixed in 10% buffered formalin to be cut for histological examination. The tissues were homogenized in 10 mL of PBS, serially diluted, and plated in triplicate. Colonies were counted after 3 days incubation at 37° C. under an atmosphere of 10% $CO_2$. Bacterial loads in the peptide-treated animals were compared to the diluent controls. Percent bacterial reduction was determined by subtracting the total number of organisms in the treated spleens from the total number of organisms in the control spleens. This difference was divided by the total number of organisms in the control spleens and multiplied by 100. The results are presented in Table 3 and discussed below.

TABLE 3

Peptide-Mediated *B. abortus* Reductions in Chronically Infected BALB/c Mice.

| Treatment (dose) | % Bacterial Reduction | Significance[a] |
|---|---|---|
| Ai-14 (500 μg) SEQ ID No. 2 | 73 | <0.05 |
| Ai-11 (500 μg) SEQ ID No. 3 | 63 | <0.05 |
| Ai-11-ac (500 μg) SEQ ID No. 3 | 30 | <0.05 |
| Ch-13 (100 μg) SEQ ID No. 6 | 33 | NS |
| Ch-10 (100 μg) SEQ ID No. 7 | 0 | NS |
| Pi-10 (500 μg) SEQ ID No. 8 | 90 | <0.05 |
| Pi-10-ac (500 μg) SEQ ID No. 8 | 0 | NS |

TABLE 3-continued

Peptide-Mediated *B. abortus* Reductions in Chronically Infected BALB/c Mice.

| Treatment (dose) | % Bacterial Reduction | Significance[a] |
|---|---|---|
| Ipi-10 (500 μg) SEQ ID No. 9 | 55 | NS |
| Ipi-10-ac (500 μg) SEQ ID No. 9 | 0 | NS |
| A1-14 (1 mg) SEQ ID No. 1 | −6 | NS |

[a]NS means not significant ($p > 0.05$).

Non-infected mice were unharmed by the injection of the peptides, but infected mice treated with a single 500 μg dose of Ch-10 (SEQ ID No. 7), Ch-13 (SEQ ID No. 6), or Pi-10-Ac (SEQ ID No. 8) died immediately after treatment. Infected mice treated with a 500 μg dose of Ipi-10 (SEQ ID No. 9) or Ipi-10-Ac (SEQ ID No. 9) did not die, but showed physiological signs of stress. No other peptides caused stress or death.

As shown in Table 3, a 500 μg dose of Pi-10 (SEQ ID No. 8) and the Ai peptides (SEQ ID Nos. 2 and 3) significantly reduced bacterial load compared to controls. Infected mice treated with 100 μg of Ch-10 (SEQ ID No. 7) or Ch-13 (SEQ ID No. 6) lived, but showed no significant reduction in bacterial infection compared to controls. (Infected mice treated with 100 μg of the Ai series showed a numerical reduction compared to the control, but the reduction was not statistically significant.)

Without wishing to be bound by this theory, it is believed that in vivo the peptides selectively lysed the infected macrophages, exposing *Brucella* to the humoral and cellular immune responses, which then destroyed the exposed bacteria.

The infected mice were generally more susceptible to peptide toxicity than were normal mice. The toxic symptoms in infected mice differed from those observed in control mice. None of the control mice died at the highest concentrations of peptides containing α-aminoisobutyric acid (Aib).

The percent bacterial reduction was increased by administering a human-gram equivalent therapeutic dose of the antibiotic, oxytetracycline, for three days to the mice, in addition to the injected peptide.

The more hydrophobic peptides containing α-aminocyclohexanecarboxylic acid (Ch) were much more toxic; these peptides maybe shortened to as few as seven amino acids to reduce toxicity while retaining activity. The peptides were more toxic in infected mice, with a pathology consistent with toxic shock syndrome. The mice died in less than 2 minutes following injection into the tail vein, and necropsy showed massive internal bleeding with the lungs filled with blood. This phenomenon was attributed to a large population of the infected macrophages being destroyed simultaneously, spilling out nitric oxide, tumor necrosis factor, and other inflammatory cytokines/mediators, thus overwhelming the organs of the mice.

In Vitro Effects on Normal and Infected Macrophages

In vitro peptide testing on infected and non-infected macrophages showed selective destruction of infected macrophages. Normal macrophage mortality was measured after exposure to various concentrations of peptides. Murine macrophages were harvested as described by Jones et al., "Survival of Virulent and Attenuated Strains of *Brucella abortus* in Normal and Gamma Interferon-Activated Murine Peritoneal Macrophages," Infection and Immunity, vol. 60, pp. 3011–3014 (1992). Following euthanasia, cells were harvested by lavage from the peritoneal cavity of ten-week old BALB/c mice using 8 mL of DMEM (Dulbecco's Modified Eagle Medium)+5% fetal calf serum (FCS) and 5 U/mL of heparin and cultured in 96 well plates at a concentration of $1.5 \times 10^5$ per well in 200 µL of DMEM+5% FCS at 37° C. with 5% $CO_2$. Cell cultures were enriched for macrophages by washing away non-adherent cells after overnight incubation with phosphate buffered saline (PBS)+ 0.5% FCS, and 200 µL of fresh media was added to the cultures.

Normal macrophages were treated with various concentrations of peptides to determine peptide toxicity levels. The cells were incubated for 1 hour at 37° C., 5% $CO_2$ in Minimum Essential Media (MEM) without FCS. The cells were washed with MEM and treated with 0.04% trypan blue, which stained the dead cells blue. Approximately 150–200 cells were counted per coverslip. Saline treatment controls gave 92.7±6.1% survival of the original macrophage population. The minimal peptide concentration that showed any macrophage toxicity for most peptides was 10 µM. The results are presented in Table 4.

TABLE 4

Normal Macrophage Survival Rates at Various Peptide Concentrations.

| Peptide | 50 µM | 10 µM | 1 µM | 0.1 µM |
|---|---|---|---|---|
| Ai-11 SEQ ID No. 3 | 56.6% | 81% | 89% | 88% |
| Ai-11-ac SEQ ID No. 3 | 58.5% | 86% | 82% | 92% |
| Ai-14 SEQ ID No. 2 | 57% | 88% | 88% | 91% |
| Pi-10 SEQ ID No. 8 | 68% | 90% | 89% | 95% |
| Pi-10-ac SEQ ID No. 8 | 49% | 88% | 89% | 92% |

Normal macrophage and infected macrophage mortality was measured as a function of peptide concentration. Murine macrophages were harvested and infected with virulent *B. abortus*, strain 2308. *B. abortus* opsonized with a sub-agglutinating dilution (1:2000) of hyperimmune BALB/c mouse sera in DMEM+5% FCS was added to the macrophages at a ratio of approximately 100 bacteria per macrophage. Phagocytosis was allowed to proceed for 2 h at 37° C. Extracellular bacteria were then removed by washing 3 times with PBS+0.5% FCS.

Using non-cytotoxic concentrations as determined above (10 µM), peptides were added to infected and noninfected cell cultures for 1 hour at 37° C., 5% $CO_2$. The cells were then washed 3 times with PBS+0.5% FCS to remove any residual peptide. Percent viability was determined as described above.

Two hours post-infection the macrophages were washed with MEM. Counts of viable *B. abortus* were made to determine the degree of macrophage infection. Approximately 30–50% of the macrophages were actually infected with *B. abortus*. The cells were separately treated with 10 µM of each peptide to be tested. The cells were incubated for one hour, washed with MEM, and treated with 0.04% trypan blue. Approximately 150–200 cells were counted per coverslip. *Brucella* infection of the macrophages had no significant effect on the macrophage population for up to 48 hours; 92.0±2.7% of the macrophage population remained viable compared to the saline control of 92.7±6.1%.

Peptide treatment of normal macrophages had no significant effect at 10 µM, except for a small effect for Ai-11 (SEQ ID No. 3) and Ai-11-ac (SEQ ID No. 3). Peptide treatment (10 µM) of infected macrophages caused significantly greater cell death compared to non-infected macrophages, with $p \leq 0.01$ compared to saline controls, for all peptides tested. The results are presented below in Table 5.

TABLE 5

Normal Macrophage and Infected Macrophage Survival Rates When Incubated with 10 µM Peptide

| [Peptide] = 10 µM | Normal Macrophage | Infected Macrophage | P Value |
|---|---|---|---|
| Ai-11 SEQ ID No. 3 | 81.0 ± 1.00 | 38.0 ± 1.00 | 0.001 |
| Ai-11-ac SEQ ID No. 3 | 86.0 ± 1.00 | 63.0 ± 1.00 | 0.001 |
| Ai-14 SEQ ID No. 2 | 86.7 ± 0.58 | 54.3 ± 1.53 | 0.001 |
| Pi-10 SEQ ID No. 8 | 90.0 ± 1.00 | 55.0 ± 1.00 | 0.001 |
| Pi-10-ac SEQ ID No. 8 | 86 ± 1.00 | 62 ± 2.00 | 0.003 |

Resistance to Trypsin

Various synthetic peptides and natural lytic peptides were tested for resistance to trypsin, a major protease in the mammalian digestive tract. Stock solutions of trypsin (Sigma Chemical Co.) type 11-s, 100 µg/mL, were diluted with water and mixed with an equal volume of solution containing the peptide, 1024 µg/mL. All samples were incubated for 20 min at 37° C. After incubation, MIC assays were performed with *E. coli*. For the peptides Ai-14 (SEQ ID No. 2), Ai-11 (SEQ ID No. 3), Ai-11-ac (SEQ ID No. 3), Ch-13 (SEQ ID No. 6), Ch-10 (SEQ ID No. 7), Pi-10 (SEQ ID No. 8), and Ipi-10 (SEQ ID No. 9), incubation with trypsin for 20 min did not decrease antibacterial activity. For the natural peptides cecropin B and magainin 2, incubation with trypsin destroyed antibacterial activity.

Thus the novel synthetic peptides may be taken orally because of their resistance to proteolytic digestion by trypsin.

The peptides of this invention may be administered to humans or other mammals in pharmaceutical compositions or formulations in combination with one or more pharmaceutically acceptable carriers known in the art. The peptides may also be administered as pharmaceutically acceptable salts. Suitable pharmaceutical adjuvants for injection solutions include stabilizing agents, solubilizing agents, buffers, and viscosity regulators. These injectable solutions may be injected intramuscularly, intraperitoneally, or intravenously. Because the peptides of this invention are resistant to proteases, oral administration is preferred in situations where oral administration is practical. Suitable pharmaceutical adjuvants for oral administration include stabilizing agents, solubilizing agents, buffers, fillers, flavorants, and coatings. The peptides may also be administered topically. Suitable adjuvants for topical application include stabilizing agents and solubilizing agents.

Without limiting the scope of the invention, examples of intracellular pathogens against which these peptides are effective include the following: various other bacterial pathogens (e.g., *Brucella* sp., *Brucella abortus*, *Brucella suis*, *Brucella melitensis*, *Mycobacterium* sp., *Mycobacterium lepraemurum*, *Mycobacterium tuberculosis*, *Salmo-* nella sp., *Salmonella typhimurium, Listeria, Shigella flexneri, Rickettsia tsutsugamushi, Rickettsia prowazekii, Rickettsia rickettsii, Chlamydia psittaci, Chlamydia trachomatis, Chlamydia pneumoniae, Coxiella burnettii, Yersinia sp., Yersinia pestis, Legionella pneumonophia, Francisella*); various mycotic pathogens (e.g., *Blastomyces* sp., *Blastomyces dermatitides, Histoplasma* sp., *Histoplasma capsulatum, Coccidioides, Cryptococcus neoformans*); various protozoal pathogens (e.g., *Leishmania* spp., *Leishmania donovani, Leishmania mexicani, Trypanosoma* sp., *Trypanosoma cruzi, Toxoplasma* sp., *Toxoplasma gondi, Plasmodium, Babesia, Theileria, Isospora*, and *Eimeria*); and various viral pathogens.

In the specification and claims, a concentration or amount of peptide is considered to be "therapeutically effective" if it reduces the level of bacterial infection to a statistically significant degree; or if it preferentially lyses infected macrophages over normal macrophages to a statistically significant degree.

The complete disclosures of all references cited in this specification are hereby incorporated by reference. Also incorporated by reference are the complete disclosures of the following three papers: Yokum et al., "Antimicrobial $\alpha,\alpha$-Dialkylated Amino Acid Rich Peptides with In-Vivo Activity against an Intracellular Pathogen," Journal of Medicinal Chemistry, vol. 39, no. 19, pp. 3603–3605 (1996); Wysong et al., "4-Aminopiperidine-4-carboxylic Acid: A Cyclic $\alpha,\alpha$-Disubstituted Amino Acid for Preparation of Water-Soluble Highly Helical Peptides," Journal of Organic Chemistry, vol. 61, no. 22, pp. 7650–7651 (1996); and Yokum et al., "Solvent Effects on the $3_{10}$-/$\alpha$-Helix Equilibrium in Short Amphipathic Peptides Rich in $\alpha,\alpha$-Disubstituted Amino Acids," Journal of the American Chemical Society, vol. 119, pp. 1167–1168 (1997). Also incorporated by reference is the complete disclosure of the co-pending patent application of McLaughlin et al., "Amphipathic Peptides," Ser. No. 08/232,525, filed Apr. 22, 1994. In the event of an otherwise irreconcilable conflict, however, the present specification shall control.

We claim:

1. A synthetic peptide comprising 6 to 15 amino acid residues, wherein:
   (a) said peptide comprises about 50% to about 100% α,α-dialkylated amino acid residues;
   (b) said peptide comprises about 25% to about 50% polar amino acid residues such that said polar residues have an overall positive charge under physiological conditions;
   (c) said peptide comprises about 50% to about 75% nonpolar α,α-dialkylated amino acid residues; and
   (d) said nonpolar residues and said polar residues are distributed within said peptide such that under physiologic conditions said peptide forms an $3_{10}$-helix, said nonpolar residues lie on one face of the $3_{10}$-helix, and said polar residues lie on the opposite face of the $3_{10}$-helix, whereby the peptide is amphipathic.

2. A peptide as recited in claim 1, wherein said peptide comprises 6 to 10 amino acid residues.

3. A peptide as recited in claim 1, wherein said polar residues are all positively charged amino acid residues.

4. A peptide as recited in claim 1, wherein said nonpolar α,α-dialkylated amino acid residues are selected from the group consisting of α-aminoisobutyric acid, 1-amino-1-cyclohexanecarboxylic acid, isovaline, di-ethyl glycine, di-n-propyl glycine, Cα-methylvaline, Cα-methylleucine, 1-amino-cyclopropanecarboxylic acid, 1-amino-cyclobutanecarboxylic acid, 1-amino-cyclopentanecarboxylic acid, 1-amino-cyclohexanecarboxylic acid, 1-amino-cycloheptanecarboxylic acid, and 1-amino-cyclooctanecarboxylic acid; and said polar residues are selected from the group consisting of lysine, arginine, histidine, 4-aminopiperidine-4-carboxylic acid, 1-amino-4-(N-ethylamino)cyclohexanecarboxylic acid, 1-amino-4-(N-butylamino)cyclohexanecarboxylic acid, 1-amino-4-(N-phenylmethylamino) cyclohexanecarboxylic acid, and 1-amino-4-(N-2-naphthylmethylamino)cyclohexanecarboxylic acid.

5. A peptide as recited in claim 1, wherein said nonpolar α,α-dialkylated amino acids are α-aminoisobutyric acid and said polar residues are selected from the group consisting of lysine and 4-aminopiperidine-4-carboxylic acid.

6. A peptide as recited in claim 1, wherein said peptide has the sequence ApiAibAibLysAibAibLysAibAibApi (SEQ ID No. 9).

7. A method for treating a bacterial infection in a mammal, comprising administering a therapeutically effective amount of a synthetic peptide comprising 6 to 15 residues, wherein:
   (a) said peptide comprises about 50% to about 100% α,α-dialkylated amino acid residues;
   (b) said peptide comprises about 25% to about 50% polar amino acid residues such that said polar residues have an overall positive charge under physiological conditions;
   (c) said peptide comprises about 50% to about 75% nonpolar α,α-dialkylated amino acid residues; and
   (d) said nonpolar residues and said polar residues are distributed within said peptide such that under physiologic conditions said peptide forms an $3_{10}$-helix, said nonpolar residues lie on one face of the $3_{10}$-helix, and said polar residues lie on the opposite face of the $3_{10}$-helix, whereby the peptide is amphipathic.

8. A method as recited in claim 7, wherein said peptide is administered by injection.

9. A method as recited in claim 7, wherein said peptide is administered orally.

10. A method as recited in claim 7, wherein said peptide is administered topically.

11. A method as recited in claim 7, wherein said peptide comprises 6 to 10 amino acid residues.

12. A peptide as recited in claim 7, wherein said polar residues are all positively charged amino acid residues.

13. A method as recited in claim 7, wherein said nonpolar α,α-dialkylated amino acid residues are selected from the group consisting of α-aminoisobutyric acid, 1-amino-1-cyclohexanecarboxylic acid, isovaline, di-ethyl glycine, di-n-propyl glycine, Cα-methylvaline, Cα-methylleucine, 1-amino-cyclopropanecarboxylic acid, 1-amino-cyclobutanecarboxylic acid, 1-amino-cyclopentanecarboxylic acid, 1-amino-cyclohexanecarboxylic acid, 1-amino-cycloheptanecarboxylic acid, and 1-amino-cyclooctanecarboxylic acid; and said polar residues are selected from the group consisting of lysine, arginine, histidine, 4-aminopiperidine-4-carboxylic acid, 1-amino-4-(N-ethylamino)cyclohexanecarboxylic acid, 1-amino-4-(N-butyl-amino)cyclohexanecarboxylic acid, 1-amino-4-(N-phenylmethylamino) cyclohexanecarboxylic acid, and 1-amino-4-(N-2-naphthylmethylamino)cyclohexanecarboxylic acid.

14. A method as recited in claim 7, wherein said nonpolar α,α-dialkylated amino acids are α-aminoisobutyric acid and said polar residues are selected from the group consisting of lysine and 4-aminopiperidine-4-carboxylic acid.

15. A method as recited in claim 7, wherein said peptide has the sequence ApiAibAibLysAibAibLysAibAibApi (SEQ ID No. 9).

16. A method for treating an infection by an intracellular pathogen in a mammal, comprising administering to the mammal a therapeutically effective amount of a synthetic peptide comprising 6 to 15 amino acid residues, wherein:
   (a) said peptide comprises about 50% to about 100% α,α-dialkylated amino acid residues;
   (b) said peptide comprises about 25% to about 50% polar amino acid residues such that said polar residues have an overall positive charge under physiological conditions;
   (c) said peptide comprises about 50% to about 75% nonpolar α,α-dialkylated amino acid residues; and
   (d) said nonpolar residues and said polar residues are distributed within said peptide such that under physiologic conditions said peptide forms an $3_{10}$-helix, said nonpolar residues lie on one face of the $3_{10}$-helix, and said polar residues lie on the opposite face of the $3_{10}$-helix, whereby the peptide is amphipathic.

17. A method as recited in claim 16, wherein said intracellular pathogen is *Brucella abortus*, and wherein said mammal is not a human.

18. A method as recited in claim 16, wherein said peptide is administered by injection.

19. A method as recited in claim 16, wherein said peptide is administered orally.

20. A method as recited in claim 16, wherein said peptide is administered topically.

21. A method as recited in claim 16, wherein said peptide comprises 6 to 10 amino acid residues.

22. A method as recited in claim 16, wherein said polar residues are all positively charged amino acid residues.

23. A peptide as recited in claim 16, wherein said nonpolar α,α-dialkylated amino acid residues are selected from the group consisting of α-aminoisobutyric acid, 1-amino-1-cyclohexanecarboxylic acid, isovaline, di-ethyl glycine, di-n-propyl glycine, Cα-methylvaline, Cα-methylleucine, 1-amino-cyclopropanecarboxylic acid, 1-amino-cyclobutanecarboxylic acid, 1-amino-cyclopentanecarboxylic acid, 1-amino-cyclohexanecarboxylic acid, 1-amino-cycloheptanecarboxylic acid, and 1-amino-cyclooctanecarboxylic acid; and said polar residues are selected from the group consisting of lysine, arginine, histidine, 4-aminopiperidine-4-carboxylic acid, 1-amino-4-(N-ethylamino)cyclohexanecarboxylic acid, 1-amino-4-(N-butylamino)cyclohexanecarboxylic acid, 1-amino-4-(N-phenylmethylamino) cyclohexanecarboxylic acid, and 1-amino-4-(N-2-naphthylmethylamino)cyclohexanecarboxylic acid.

24. A peptide as recited in claim 16, wherein said nonpolar α,α-dialkylated amino acids are α-aminoisobutyric acid and said polar residues are selected from the group consisting of lysine and 4-aminopiperidine-4-carboxylic acid.

25. A peptide as recited in claim 16, wherein said peptide has the sequence ApiAibAibLysAibAibLysAibAibApi (SEQ ID No. 9).

26. A method for lysing mammalian macrophages infected with an intracellular pathogen, wherein the infected macrophages are located in the presence of uninfected macrophages and wherein the infected macrophages are preferentially lysed in greater proportion than the uninfected macrophages, comprising administering to the macrophages a therapeutically effective amount of a synthetic peptide comprising 6 to 15 amino acid residues, wherein:
  (a) said peptide comprises about 50% to about 100% α,α-dialkylated amino acid residues;
  (b) said peptide comprises about 25% to about 50% polar amino acid residues such that said polar residues have an overall positive charge under physiological conditions;
  (c) said peptide comprises about 50% to about 75% nonpolar α,α-dialkylated amino acid residues; and
  (d) said nonpolar residues and said polar residues are distributed within said peptide such that under physiologic conditions said peptide forms an $3_{10}$-helix, said nonpolar residues lie on one face of the $3_{10}$-helix, and said polar residues lie on the opposite face of the $3_{10}$-helix, whereby the peptide is amphipathic.

27. A method as recited in claim 26, wherein said intracellular pathogen is *Brucella abortus*.

28. A method as recited in claim 26, wherein said peptide comprises 6 to 10 amino acid residues.

29. A peptide as recited in claim 26, wherein said polar residues are all positively charged amino acid residues.

30. A method as recited in claim 26, wherein said nonpolar α,α-dialkylated amino acid residues are selected from the group consisting of α-aminoisobutyric acid, 1-amino-1-cyclohexanecarboxylic acid, isovaline, di-ethyl glycine, di-n-propyl glycine, Cα-methylvaline, Cα-methylleucine, 1-amino-cyclopropanecarboxylic acid, 1-amino-cyclobutanecarboxylic acid, 1-amino-cyclopentanecarboxylic acid, 1-amino-cyclohexanecarboxylic acid, 1-amino-cycloheptanecarboxylic acid, and 1-amino-cyclooctanecarboxylic acid; and said polar residues are selected from the group consisting of lysine, arginine, histidine, 4-aminopiperidine-4-carboxylic acid, 1-amino-4-(N-ethylamino)cyclohexanecarboxylic acid, 1-amino-4-(N-butylamino)cyclohexanecarboxylic acid, 1-amino-4-(N-phenylmethylamino) cyclohexanecarboxylic acid, and 1-amino-4-(N-2-naphthylmethylamino)cyclohexanecarboxylic acid.

31. A method as recited in claim 26, wherein said nonpolar α,α-dialkylated amino acids are α-aminoisobutyric acid and said polar residues are selected from the group consisting of lysine and 4-aminopiperidine-4-carboxylic acid.

32. A method as recited in claim 26, wherein said peptide has the sequence ApiAibAibLysAibAibLysAibAibApi (SEQ ID No. 9).

33. A peptide as recited in claim 1, wherein said peptide is acetylated at the N-terminus.

34. A peptide as recited in claim 6, wherein said peptide is acetylated at the N-terminus.

35. A method as recited in claim 7, wherein said peptide is acetylated at the N-terminus.

36. A method as recited in claim 15, wherein said peptide is acetylated at the N-terminus.

37. A method as recited in claim 16, wherein said peptide is acetylated at the N-terminus.

38. A method as recited in claim 25, wherein said peptide is acetylated at the N-terminus.

39. A method as recited in claim 26, wherein said peptide is acetylated at the N-terminus.

40. A method as recited in claim 32, wherein said peptide is acetylated at the N-terminus.

* * * * *

UNITED STATES PATENT AND TRADEMARK OFFICE
CERTIFICATE OF CORRECTION

PATENT NO.        : 7,262,163 B2
APPLICATION NO.   : 10/414342
DATED             : August 28, 2007
INVENTOR(S)       : Mark L. McLaughlin et al.

It is certified that error appears in the above-identified patent and that said Letters Patent is hereby corrected as shown below:

Replace paragraph at column 1, lines 10-13:

--The development of this invention was partially funded by the Government under grant NSF OSR-9108765 (1992-96)-ADP-01 awarded by the National Science Foundation. The Government has certain rights in this invention.--

Signed and Sealed this

Fourth Day of December, 2007

JON W. DUDAS
*Director of the United States Patent and Trademark Office*